United States Patent
Fischetti et al.

(10) Patent No.: US 9,914,916 B2
(45) Date of Patent: *Mar. 13, 2018

(54) DIMERIC BACTERIOPHAGE LYSINS

(71) Applicant: THE ROCKEFELLER UNIVERSITY, New York, NY (US)

(72) Inventors: Vincent A. Fischetti, West Hempstead, NY (US); Gregory Resch, Evian les bains (FR)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/007,445

(22) Filed: Jan. 27, 2016

(65) Prior Publication Data

US 2016/0208231 A1 Jul. 21, 2016

Related U.S. Application Data

(63) Continuation of application No. 14/349,736, filed as application No. PCT/US2012/058717 on Oct. 4, 2012, now Pat. No. 9,279,118.

(60) Provisional application No. 61/543,803, filed on Oct. 5, 2011.

(51) Int. Cl.
| | | |
|---|---|---|
| *A61K 38/46* | (2006.01) | |
| *C12N 9/80* | (2006.01) | |
| *C07H 21/04* | (2006.01) | |
| *C07K 1/00* | (2006.01) | |
| *C12N 9/36* | (2006.01) | |
| *C07K 14/005* | (2006.01) | |
| *A01N 63/00* | (2006.01) | |
| *A01N 63/02* | (2006.01) | |
| *C12N 7/00* | (2006.01) | |
| *A61K 38/47* | (2006.01) | |
| *C12N 9/24* | (2006.01) | |
| *A61K 38/00* | (2006.01) | |

(52) U.S. Cl.
CPC ......... *C12N 9/2462* (2013.01); *A01N 63/00* (2013.01); *A01N 63/02* (2013.01); *A61K 38/47* (2013.01); *C07K 14/005* (2013.01); *C12N 7/00* (2013.01); *C12N 9/2405* (2013.01); *C12N 9/80* (2013.01); *A61K 38/00* (2013.01); *C07K 2319/00* (2013.01); *C12N 2795/10022* (2013.01); *C12N 2795/10033* (2013.01); *C12N 2795/10071* (2013.01); *C12Y 302/01017* (2013.01)

(58) Field of Classification Search
CPC ............ C07K 14/005; C07K 2319/00; C12N 2795/10071; C12N 2795/10033; C12N 9/80; C12N 2795/10022; A01N 63/00
USPC ......... 424/94.6; 435/228; 536/23.2; 530/350
See application file for complete search history.

(56) References Cited

U.S. PATENT DOCUMENTS

| | | |
|---|---|---|
| 5,604,109 A | 2/1997 | Fischetti et al. |
| 5,985,271 A | 11/1999 | Fischetti et al. |
| 6,017,528 A | 1/2000 | Fischetti et al. |
| 6,056,955 A | 5/2000 | Fischetti et al. |
| 6,248,324 B1 | 6/2001 | Fischetti et al. |
| 6,254,866 B1 | 7/2001 | Fischetti et al. |
| 6,264,945 B1 | 7/2001 | Fischetti et al. |
| 7,402,309 B2 | 7/2008 | Fischetti et al. |
| 7,569,223 B2 | 8/2009 | Fischetti et al. |
| 7,582,291 B2 | 9/2009 | Yoong et al. |
| 7,638,600 B2 | 12/2009 | Fischetti et al. |
| 9,279,118 B2 * | 3/2016 | Fischetti ............. C07K 14/005 |
| 2002/0136712 A1 | 9/2002 | Vincent et al. |
| 2003/0171552 A1 | 9/2003 | Weidanz et al. |
| 2008/0221035 A1 | 9/2008 | Fischetti et al. |

FOREIGN PATENT DOCUMENTS

| | | |
|---|---|---|
| WO | WO2002102405 | 12/2002 |
| WO | WO2004058182 | 7/2004 |
| WO | WO2008018854 | 2/2008 |
| WO | WO2010002959 | 1/2010 |
| WO | WO2010020657 | 2/2010 |

OTHER PUBLICATIONS

Beres, SB et al (2007) Contribution of exogenous genetic elements to the group A *Streptococcus* metagenome Plos One 2(8):1-14 e800.
Borysowski, J et al (2006) Bacteriophage endolysins as a novel class of antibacterial agents Exp Biol Med 231(4):366-377.
Dixon, RE et al (1968) Lysostaphin: an enzymatic approach to staphylococcal disease. 3. Combined lysostaphin-methicillin therapy of established staphylococcal abscesses in mice Yale J Biol Med 41(1):62-68.
Entenza, JM et al (2005) Therapeutic effects of bacteriophage Cpl-1 lysin against *Streptococcus pneumoniae* endocarditis in rats Antimicrob Agents Chemother 49(11):4789-4792.
Fernandez-Tornero, C et al (2002) Two new crystal forms of the choline-binding domain of the major pneumococcal autolysin: insights into the dynamics of the active homodimer J Mol Biol 321(1):163-173.
Fischetti, VA (2008) Bacteriophage lysins as effective antibacterials Curr Opin Microbiol 11(5):393-400.
Garcia, JL et al (1987) Cloning, purification, and biochemical characterization of the pneumococcal bacteriophage Cp-1 lysin J Virol 61(8):2573-2580.
Garcia, E et al (1988) Molecular evolution of lytic enzymes of *Streptococcus pneumoniae* and its bacteriophages Proc Natl Acad Sci USA 85(3):914-918.

(Continued)

*Primary Examiner* — Ganapathirama Raghu

(74) *Attorney, Agent, or Firm* — Klauber & Jackson LLC

(57) ABSTRACT

The present invention provides isolated dimeric *Streptococcus*-specific phage lysins having two *Streptococcus*-specific phage lysin monomers covalently linked to each other, and having killing activity against one or more *Streptococcus* bacteria. Also provided for are pharmaceutical compositions of dimeric lysins and their use in therapeutic treatment or alleviation of infections or bacterial colonizations. The dimeric lysins may also be used to decontaminate porous and non-porous surfaces or devices.

20 Claims, 7 Drawing Sheets

(56) References Cited

OTHER PUBLICATIONS

Garcia, P et al (1990) Modular organization of the lytic enzymes of *Streptococcus pneumoniae* and its bacteriophages Gene 86(1):81-88.
Garcia, P et al (1997) Bacteriophages of *Streptococcus pneumoniae*: a molecular approach Microb Drug Resist 3 (2):165-176.
Grandgirard, D et al (2008) Phage lytic enzyme Cpl-1 for antibacterial therapy in experimental pneumococcal meningitis J Infect Dis 197(11):1519-1522.
Jado, I et al (2003) Phage lytic enzymes as therapy for antibiotic-resistant *Streptococcus pneumoniae* infection in a murine sepsis model J Antimicrob Chemother 52(6):967-973.
Loeffler, JM et al (2001) Rapid killing of *Streptococcus pneumoniae* with a bacteriophage cell wall hydrolase Science 294(5549):2170-2172.
Loeffler, J.M. et al (2003) Synergistic lethal effect of a combination of phage lytic enzymes with different activities on penicillin-sensitive and -resistant *Streptococcus pneumoniae* strains Antimicrob Agents Chemother 47(1):375-377.
Loeffler, JM et al (2003) Phage lytic enzyme Cpl-1 as a novel antimicrobial for pneumococcal bacteremia Infect Immun 71(11):6199-6204.
Loessner, MJ et al (1995) Heterogeneous endolysins in Listeria monocytogenes bacteriophages: a new class of enzymes and evidence for conserved holin genes within the siphoviral lysis cassettes Mol Microbiol 16(6):1231-1241.
Loessner, MJ et al (1996) Modified Listeria bacteriophage lysin genes (ply) allow efficient overexpression and one-step purification of biochemically active fusion proteins Appl Environ Microbiol 62(8):3057-3060.
Loessner, MJ et al (1999) Evidence for a holin-like protein gene fully embedded out of frame in the endolysin gene of *Staphylococcus aureus* bacteriophage 187 J Bacteriol 181(15):4452-4460.
Lopez, R et al (1992) Structural analysis and biological significance of the cell wall lytic enzymes of *Streptococcus pneumoniae* and its bacteriophage FEMS Microbial Lett 100(1-3):439-448.
Lopez, R et al (1997) The pneumococcal cell wall degrading enzymes: a modular design to create new lysins? Microb Drug Resist 3(2):199-211.
Nelson, D et al (2001) Prevention and elimination of upper respiratory colonization of mice by group A streptococci by using a bacteriophage lytic enzyme PNAS 98(7):4107-4112.
Perez-Dorado, I et al (2007) Elucidation of the molecular recognition of bacterial cell wall by modular pneumococcal phage endolysin CPL-1 J Biol Chem 282(34):24990-24999.
Romero, A et al (1990) Sequence of the *Streptococcus pneumoniae* bacteriophage HB-3 amidase reveals high homology with the major host autolysin J Bacteriol 172(9):5064-5070.

Romero, P et al (2004) Characterization of LytA-like N-acetylmuramoyl-L-alanine amidases from two new *Streptococcus mitis* bacteriophages provides insights into the properties of the major pneumococcal autolysin J Bacteriol 186(24):8229-8239.
Romero, P et al (2007) Key role of amino acid residues in the dimerization and catalytic activation of the autolysin LytA, an important virulence factor in Streptococcus pneumonia J Biol Chem 282(24):17729-17737.
Ronda, C et al (1987) Biological role of the pneumococcal amidase. Cloning of the lytA gene in *Streptococcus pneumonia* Eur J Biochem 164(3):621-624.
Sanchez-Puelles, JM et al (1987) 3'-end modifications of the Streptococcus pneumoniae lytA gene: role of the carboxy terminus of the pneumococcal autolysin in the process of enzymatic activation (conversion) Gene 61(1):13-19.
Sulakvelidze, A et al (2001) Bacteriophage therapy Antimicrob Agents Chemother 45(3):649-659.
Sulakvelidze, A and Barrow, P (2005) Phage therapy in animals and agribusiness, in E. Kutter and A. Sulakvelidze (ed.) Bacteriophages: Biology and Applications CRC Press, USA 335-371.
Sulakvelidze, A and Kutter, E (2005) Bacteriophage therapy in humans, in E. Kutter and A. Sulakvelidze (ed.), Bacteriophages: Biology and Applications CRC Press, USA 381-426.
Varea, J et al (2000) Do sequence repeats play an equivalent role in the choline-binding module of pneumococcal LytA amidase? J Biol Chem 275(35):26842-26855.
Wang, IN et al (2000) Holins: the protein clocks of bacteriophage infections Annu Rev Microbiol 54:799-825.
Witzenrath, M et al (2009) Systemic use of the endolysin Cpl-1 rescues mice with fatal pneumococcal pneumonia Crit Care Med 37(2):642-649.
Young, I et al (2000) Phages will out: strategies of host cell lysis Trends Microbiol 8(3):120-128.
Djurkovic, S et al (2005) Synergistic killing of *Streptococcus pneumoniae* with the bacteriophage lytic enzyme Cpl-1 and penicillin or gentamicin depends on the level of penicillin resistance Antimicrob Agents Chemother 49(3):1225-1228.
Monterroso, B et al (2008) Insights into the structure-function relationships of pneumococcal cell wall lysozymes, LytC and Cpl-1 J Biol Chem 283(42):28618-28628.
Resch, G et al (2009) Amer Soc Microbiology Meeting Abstracts, vol. 109, 21 May 2009, pp. 1-2, XP008176318.
Resch, G et al (2011) Abstracts Book, Interscience Conference on Antimicrobiol Agents Chemotherapy 51, Jan. 1, 2011, p. E-1828, XP008176320.
Resch, G et al (2011) PEGylating a bacteriophage endolysin inhibits its bactericidal activity AMB Express 1:29.

* cited by examiner

FIGURE 1

```
Cpl-1    MVKKNDLFVDVSSHNGYDITGILEQMGTTNTIIKISESTTYLNPCLSAQVEQSNPIGFYH  60
LytA     ------MEINVS-----KLRTDLPQVGVQPYRQVHAHSTG--NPHSTVQNEAD-----YH  42
              : ::**    .:  * *:*.        :.**   **  :.* * .      **

Cpl-1    FARFGGDVAEAEREAQFFLDNVPMQVKYLVLDYEDDPSGDAQANTNACLRFMQMIADAGY 120
LytA     WRKD-----PELGFFSHIVGNGCIMQVG-PVDNGAWDVGGGWNAETYAAVELIESHSTKEE 97
           : :        .*    :::. :.  ***    * :    * .*. :*:* *.:.::: :

Cpl-1    KPIYYSYKPFTHDNVDYQQILAQFPNSLWIAGYGLNDGTANFEYFPSMDGIRWWQYSSNP 180
LytA     FMTDYRLYIELLRNLADEAGLPKTLDTGSLAGIKTHEYCTNNQPNNHSDHVDPYPYLAK- 156
              *:      *:   *.:  ::   :**   ::   :* :      * :  : * ::

Cpl-1    FDKNIVLLDDEEDDKPKTAGTWKQDSKGWWFRRNNGSFPYNKWEKIGGVWYYFDSKGYCL 240
LytA     WGISREQFKHDIENGLTIETGWQKNDTGYWYVHSDGSYPKDKFEKINGTWYYFDSSGYML 216
         :. .    :..: :: .     *::.:.*:*:  :.:**:*  :*:***.*.******.** *

Cpl-1    TSEWLKDND-KWYYLKDNGAMATGWVLVGSEWYYMDDSGAMVTGWVKYKNNWYYMTNERG 299
LytA     ADRWRKHTDGNWYWFDNSGEMATGWKKIADKWYYFNEEGAMKTGWVKYKDTWYYLDAKEG 276
          ..* *..* :**::.:.* *****  :..:***:::.*** *******:.***;   :.*

Cpl-1    NMVSNEFIK--SGKGWYFMNTNGELADNPSFTKEPDGLITVA 339
LytA     AMVSNAFIQSADGTGWYYLKPDGTLADKPEFTVEPDGLITVK 318
         ****.**:   .*.***:::.:* ***.*.** ********
```

FIGURE 6

```
Cpl-1       MVKKNDLFVDVSSHNGYDITGILEQMGTTNTIIKISESTTYLNPCLSAQVEQSNPIGFYH    60
C45S        MVKKNDLFVDVSSHNGYDITGILEQMGTTNTIIKISESTTYLNPSLSAQVEQSNPIGFYH    60
C45S,D324C  MVKKNDLFVDVSSHNGYDITGILEQMGTTNTIIKISESTTYLNPSLSAQVEQSNPIGFYH    60

Cpl-1       FARFGGDVAEAEREAQFFLDNVPMQVKYLVLDYEDDPSGDAQANTNACLRFMQMIADAGY   120
C45S        FARFGGDVAEAEREAQFFLDNVPMQVKYLVLDYEDDPSGDAQANTNACLRFMQMIADAGY   120
C45S,D324C  FARFGGDVAEAEREAQFFLDNVPMQVKYLVLDYEDDPSGDAQANTNACLRFMQMIADAGY   120

Cpl-1       KPIYYSYKPFTHDNVDYQQILAQFPNSLWIAGYGLNDGTANFEYFPSMDGIRWWQYSSNP   180
C45S        KPIYYSYKPFTHDNVDYQQILAQFPNSLWIAGYGLNDGTANFEYFPSMDGIRWWQYSSNP   180
C45S,D324C  KPIYYSYKPFTHDNVDYQQILAQFPNSLWIAGYGLNDGTANFEYFPSMDGIRWWQYSSNP   180

Cpl-1       FDKNIVLLDDEEDDKPKTAGTWKQDSKGWWFRRNNGSFPYNKWEKIGGVWYYFDSKGYCL   240
C45S        FDKNIVLLDDEEDDKPKTAGTWKQDSKGWWFRRNNGSFPYNKWEKIGGVWYYFDSKGYCL   240
C45S,D324C  FDKNIVLLDDEEDDKPKTAGTWKQDSKGWWFRRNNGSFPYNKWEKIGGVWYYFDSKGYCL   240

Cpl-1       TSEWLKDNDKWYYLKDNGAMATGWVLVGSEWYYMDDSGAMVTGWVKYKNNWYYMTNERG   299
C45S        TSEWLKDNDKWYYLKDNGAMATGWVLVGSEWYYMDDSGAMVTGWVKYKNNWYYMTNERG   299
C45S,D324C  TSEWLKDNDKWYYLKDNGAMATGWVLVGSEWYYMDDSGAMVTGWVKYKNNWYYMTNERG   299

Cpl-1       NMVSNEFIKSGKGWYFMNTNGELADNPSFTKEPDGLITVA                      339
C45S        NMVSNEFIKSGKGWYFMNTNGELADNPSFTKEPDGLITVA                      339
C45S,D324C  NMVSNEFIKSGKGWYFMNTNGELACNPSFTKEPDGLITVA                      339
```

FIGURE 7

```
Cpl-1    MVKKNDLFVDVSSHNGYDITGILEQMGTTNTIIKISESTTYLNPCLSAQVEQSNPIGFYH  60
Pal                                                   MGVDIEKGVAWMQ  13
LytA     ------MEINVS-----KLRTDLPQVGVQPYRQVHAHSTG--NPHSTVQNEAD-----YH  42

Cpl-1    FARFGGDVAEAEREAQFFLDNVPMQVKYLVLDYEDDPSGDAQANTNACLRFMQMIADAGY  120
Pal      ARKGRVSYSMDFRDGPDSYDCSSSMYYALRSAGASSAGWAVNTEYMHAWLIENGYELISE  73
LytA     WRKD----PELGFFSHIVGNGCIMQVG-PVDNGAWDVGGGWNAETYAAVELIESHSTKEE  97

Cpl-1    KPIYYSYKPFTHDNVDYQQILAQFPNSLWIAGYGLNDGTANFEYFPSMDGIRWWQYSSNP  180
Pal      NAPWDAKRGDIFIWGRKGASAGAGGHTGMFIDSDNIIHCNYAYDGIVNDHDERWYYAGQP  134
LytA     FMTDYRLYIELLRNLADEAGLPKTLDTGSLAGIKTHEYCTNNQPNNHSDHVDPYPYLAK-  156

Cpl-1    FDKNIVLLDDEEDDKPKTAGTWKQDSKGWWFRRNNGSFPYNKWEKI--GGVWYYFDSKGYCL  240
Pal      YYYVYRLTNANAQPAEKKLG-WQKDATGFWYARANGTYPKDEFEYIEENKSWFYFDDQGYML  195
LytA     WGISREQFKHDIENGLTIETGWQKNDTGYWYVHSDGSYPKDKFEKI--NGTWYYFDSSGYML  216
                                  *     *  *      *  *     *  ***   ** *

Cpl-1    TSEWLKDND-KWYYLKDNGAMATGWVLVGSEWYYMDDSGAMVTGWVKYKNNWYYMTNERG  299
Pal      AEKWLKHTDGNWYWFDRDGYMATSWKRIGESWYYFNRDGSMVTGWIKYYDNWYYCDATNG  255
LytA     ADRWRKHTDGNWYWFDNSGEMATGWKKIADKWYYFNEEGAMKTGWVKYKDTWYYLDAKEG  276
           *  *  **    * *** *         ***    *  * ***  **    ***   *

Cpl-1    NMVSNEFIK--SGKGWYFMNTNGELADNPSFTKEPDGLITVA   339
Pal      DMKSNAFIR--YNDGWYLLLPDGRLADKPQFTVEPDGLITAKV  296
LytA     AMVSNAFIQSADGTGWYYLKPDGTLADKPEFTVEPDGLITVK   318
          * ** **      ***       *  *** * **  *******
```

DIMERIC BACTERIOPHAGE LYSINS

CROSS REFERENCE TO RELATED APPLICATIONS

The present application is a Continuation of National Stage application Ser. No. 14/349,736, filed Apr. 4, 2014, now U.S. Pat. No. 9,279,118, which claims priority from PCT Application No. PCT/US2012/058717 filed Oct. 4, 2012, which in turn, claims priority from U.S. Provisional Application Ser. No. 61/543,803 filed Oct. 5, 2011. Applicants claim the benefits of 35 U.S.C. § 120 as to the National Stage Application and the PCT Application and priority under 35 U.S.C. § 119 as to the said U.S. Provisional application, and the entire disclosures of both applications are incorporated herein by reference in their entireties.

FIELD OF THE INVENTION

The present invention relates to the generation and use of dimeric lysins to detect and kill Streptococcus bacteria, in particular mutant lysins capable of dimerization to dimeric lysins having enhanced activity and/or stability. The present invention relates to methods for the prophylactic and therapeutic amelioration, decolonization, and treatment of bacteria, particularly Streptococcus bacterial strains, and related conditions. The methods of the invention utilize dimeric phage lysins, particularly dimeric pneumococcal phage lysins, including Cpl-1 lytic enzymes and variants thereof.

BACKGROUND

A major problem in medicine has been the development of drug resistant bacteria as more antibiotics are used for a wide variety of illnesses and other conditions. Hospital infections are the $8^{th}$ leading cause of death in the United States, due in large part to drug-resistant and newly-emerging pathogens. The use of more antibiotics and the number of bacteria showing resistance has prompted longer treatment times. Furthermore, broad, non-specific antibiotics, some of which have detrimental effects on the patient, are now being used more frequently. A related problem with this increased use is that many antibiotics do not penetrate mucus linings easily. Additionally, the number of people allergic to antibiotics appears to be increasing. Accordingly, there is a commercial need for new antibacterial approaches, especially those that operate via new modalities or provide new means to kill pathogenic bacteria.

Gram-positive bacteria are surrounded by a cell wall containing polypeptides and polysaccharide. The gram-positive cell wall appears as a broad, dense wall that is 20-80 nm thick and consists of numerous interconnecting layers of peptidoglycan. Between 60% and 90% of the gram-positive cell wall is peptidoglycan, providing cell shape, a rigid structure, and resistance to osmotic shock. The cell wall does not exclude the Gram stain crystal violet, allowing cells to be stained purple, and therefore "Gram-positive." Gram-positive bacteria include but are not limited to the genera Actinomyces, Bacillus, Listeria, Lactococcus, Staphylococcus, Streptococcus, Enterococcus, Mycobacterium, Corynebacterium, and Clostridium. Medically relevant species include Streptococcus pyogenes, Streptococcus pneumoniae, Staphylococcus aureus, and Enterococcus faecalis.

Antibacterials that inhibit cell wall synthesis, such as penicillins and cephalosporins, interfere with the linking of the interpeptides of peptidoglycan and weaken the cell wall of both gram positive and gram negative bacteria. Because the peptidoglycans of gram-positive bacteria are exposed, gram-positive bacteria are more susceptible to these antibiotics. Advantageously, eukaryotic cells lack cell walls and are not susceptible to these drugs or other cell wall agents.

Attempts have been made to treat bacterial diseases through the use of bacteriophages. However, the direct introduction of bacteriophages into an animal to prevent or fight diseases has certain drawbacks. Specifically, both the bacteria and the phage have to be in the correct and synchronized growth cycles for the phage to attach. Additionally, there must be the right number of phages to attach to the bacteria; if there are too many or too few phages, there will be either no attachment or no production of the lysing enzyme. The phage must also be active enough. The phages are also inhibited by many things including bacterial debris from the organism it is going to attack. Further complicating the direct use of a bacteriophage to treat bacterial infections is the possibility of immunological reactions, rendering the phage non-functional.

Novel antimicrobial therapy approaches include enzyme-based antibiotics ("enzybiotics") such as bacteriophage lysins. Phages use these lysins to digest the cell wall of their bacterial hosts, releasing viral progeny through hypotonic lysis. A similar outcome results when purified, recombinant lysins are added externally to Gram-positive bacteria. The high lethal activity of lysins against Gram-positive pathogens makes them attractive candidates for development as therapeutics. Bacteriophage lysins were initially proposed for eradicating the nasopharyngeal carriage of pathogenic streptococci (Loeffler, I. M. et al (2001) Science 294: 2170-2172; Nelson, D. et al (2001) Proc Natl Acad Sci USA 98:4107-4112). Lysins are part of the lytic mechanism used by double stranded DNA (dsDNA) phage to coordinate host lysis with completion of viral assembly (Wang, I. N. et al (2000) Annu Rev Microbiol 54:799-825). Phage encode both holins that open a pore in the bacterial membrane, and peptidoglycan hydrolases called lysins that break bonds in the bacterial wall. Late in infection, lysin translocates into the cell wall matrix where it rapidly hydrolyzes covalent bonds essential for peptidoglycan integrity, causing bacterial lysis and concomitant progeny phage release.

Lysin family members exhibit a modular design in which a catalytic domain is fused to a specificity or binding domain (Lopez, R. et al (1997) Microb Drug Resist 3:199-21 1). Lysins can be cloned from viral prophage sequences within bacterial genomes and used for treatment (Beres, S. B. et al (2007) PLoS ONE 2(8): 1-14). When added externally, lysins are able to access the bonds of a Gram-positive cell wall (FIG. 1) (Fischetti, V. A. (2008) Curr Opinion Microbiol 11:393-400). Lysins have been shown to demonstrate a high lethal activity against numerous Gram-positive pathogens (especially the bacterium from which they were cloned), raising the possibility of their development as therapeutics (Fischetti, V. A. (2008) Curr Opinion Microbiol 11:393-400; Nelson, D. L. et al (2001) Proc Natl Acad Sci USA 98:4107-4112).

Bacteriophage lytic enzymes have been established as useful in the assessment and specific treatment of various types of infection in subjects through various routes of administration. For example, U.S. Pat. No. 5,604,109 (Fischetti et al.) relates to the rapid detection of Group A streptococci in clinical specimens, through the enzymatic digestion by a semi-purified Group C streptococcal phage associated lysin enzyme. This enzyme work became the basis of additional research, leading to methods of treating diseases. Fischetti and Loomis patents (U.S. Pat. Nos. 5,985,271, 6,017,528 and 6,056,955) disclose the use of a lysin enzyme produced by group C streptococcal bacteria infected with a CI bacteriophage. U.S. Pat. No. 6,248,324 (Fischetti and Loomis) discloses a composition for dermatological infections by the use of a lytic enzyme in a carrier suitable for topical application to dermal tissues. U.S. Pat. No. 6,254,866 (Fischetti and Loomis) discloses a method for treatment of bacterial infections of the digestive tract which comprises administering a lytic enzyme specific for the infecting bacteria. The carrier for delivering at least one lytic enzyme to the digestive tract is selected from the group consisting of suppository enemas, syrups, or enteric coated pills. U.S. Pat. No. 6,264,945 (Fischetti and Loomis) discloses a method and composition for the treatment of bacterial infections by the parenteral introduction (intramuscularly, subcutaneously, or intravenously) of at least one lytic enzyme produced by a bacteria infected with a bacteriophage specific for that bacteria and an appropriate carrier for delivering the lytic enzyme into a patient.

Phage associated lytic enzymes have been identified and cloned from various bacteriophages, each shown to be effective in killing specific bacterial strains. U.S. Pat. Nos. 7,402,309, 7,638,600 and published PCT Application WO2008/018854 provides distinct phage-associated lytic enzymes useful as antibacterial agents for treatment or reduction of *Bacillus anthracia* infections. U.S. Pat. No. 7,569,223 describes the pneumococcal phage lytic enzyme Pal for *Streptococcus pneumoniae*. Lysin useful for *Enterococcus* (*E. faecalis* and *E. faecium*, including vancomycin resistant strains) are described in U.S. Pat. No. 7,582,291. US 2008/0221035 describes mutant Ply GBS lysins highly effective in killing Group B streptococci. A chimeric lysin denoted ClyS, with activity against Staphylococci bacteria, including *Staphylococcus aureus*, is detailed in WO 2010/002959.

*Streptococcus pneumoniae* (*S. pneumoniae*), a gram-positive encapsulated diplococcus, is a primary etiologic agent in human illnesses such as bacteremia, meningitis, pneumonia, otitis media, and sinusitis. This bacterium is responsible for the death of >1 million children per year under five years of age worldwide (English, M (2000) Paediatr Respir Rev 1:21-5) and community-acquired pneumonia is the sixth most common cause of death in the USA (File, T M (2004) Am J Med 117 Suppl 3A:39S-50S). Moreover, *S. pneumoniae* is a major cause of acute otitis media worldwide, a disease that affects more than 5 million children per year in the USA (CDC (2009) Pneumococcal diseases, p. 217-30. In W. Atkinson, et al (ed.), Epidemiology and prevention of vaccine-preventable diseases (11th ed), Public Health Foundation, Washington DC). Finally, secondary infections as a result of influenza pandemics account for >90% of deaths, with *S. pneumoniae* being the leading cause of these deaths (Brundage, J F Shanks G D (2008) Emerg Infect Dis 14:1193-9; Brundage, J F Shanks G D (2007) J Infect Dis 196:1717-8; Morens, D M et al (2009) N Engl J Med 361:225-9; Morens, D M et al (2009) Public Health Rep 124:22-5). Pneumococcal infections are often treated with antibiotics, but bacteriologically confirmed treatment failures, due to the increasing incidence of resistance (Reinert, R R (2009) Clin Microbiol Infect 15 Suppl 3:1-3) were reported for macrolides, fluoroquinolones, and cephalosporins (Mandell, L A et al (2002) Clin Infect Dis 35:721-7). The overuse and misuse of antibiotics as a result of treatment of millions of otitis media cases only contribute to the emergence of resistant strains (Goossens, H (2009) Clin Microbiol Infect 15 Suppl 3:12-5. Taken together, these observations have prompted the need for new drugs, acting by totally different mechanisms, for the treatment and prevention of pneumococcal associated diseases.

Prior to the discovery of antibiotics, phages, a major predator of bacteria in nature, were viewed as a possible method to control pathogenic bacteria. At the time, several reports of the successful use of phage to treat infections were published (Sulakvelidze, A and Barrow, P (2005) Phage therapy in animals and agribusiness, p. 335-71. In E. Kutter and A. Sulakvelidze (ed.), Bacteriophages: Biology and Applications, CRC Press, USA; Sulakvelidze, A and Kutter, E (2005) Bacteriophage therapy in humans, p. 381-426. In E. Kutter and A. Sulakvelidze (ed.), Bacteriophages: Biology and Applications, CRC Press, USA), but the advent of antibiotics in the 40's led to a rapid decline of phage therapy research in the western world. The past decade has seen a renewed interest in phage therapy and phage derived antibacterial compounds (Borysowski, J et al (2006) Exp Biol Med 231:366-77; Fischetti, V A (2008) Curr Opin Microbiol 11:393-400).

One of these products, phage endolysins or lysins, have been exploited for their rapid killing action on gram-positive bacteria (Borysowski, J et al (2006) Exp Biol Med 231:366-77; Fischetti, V A (2008) Curr Opin Microbiol 11:393-400). These specific enzymes are produced at the time when phage progeny need to escape the bacterial host. Pneumococcal phage Cp-1 produces the lysin Cpl-1, a 37 kDa enzyme. This lysin is constructed like all such endolysins, having two well defined domains connected by a flexible linker. The catalytic activity is restricted to the N-terminal domain, while the C-terminal part, containing 6 choline-binding repeats (ChBR) and a C-terminal tail of 13 amino-acids, is required for substrate binding in the pneumococcal cell wall. Cpl-1 belongs to the family of lysozymes which target the β1,4 linkages between N-acetylmuramic acid and N-acetyl-D-glucosamine residues in the peptidoglycan (Perez-Dorado, INE et al (2007) J Biol Chem 282:24990-9). Its choline-dependent activity makes Cpl-1 highly specific for *S. pneumonia* (Garcia, J L et al (1987) J Virol 61:2573-80). The Cpl-1 gene has been cloned into the high expression vector pin111An and then over-expressed and purified (Loeffler, J M et al (2003) Infect Immun 71:6199-204).

Purified Cpl-1 has been successfully tested for treating pneumococcal sepsis (Jado, I et al (2003) J Antimicrob Chemother 52:967-73; Loeffler, J M and Fischetti, V A (2003) Antimicrob Agents Chemother 47:375-7), endocarditis (Entenza, J M et al (2005) Antimicrob Agents Chemother 49:4789-92), pneumococcal meningitis (Grandgirard, D et al (2008) J Infect Dis 197:1519-22), and pneumonia (Witzenrath, M et al (2009) Crit Care Med 37:642-9) in rodent models. Nevertheless, proteins are usually quickly cleared in vivo and repeated injections or even continuous infusion of Cpl-1 was required in many of the studies performed to date (Entenza, J M et al (2005) Antimicrob Agents Chemother 49:4789-92. 31; Witzenrath, M et al (2009) Crit Care Med 37:642-9).

These results may be a shortcoming for the clinical development of Cpl-1 and similar lysins. What is needed in the art are improved lysins that may be used to treat pneumococcal diseases having killing activity and enhanced clinically-relevant parameters, such as longer half life or reduced clearance in vivo.

SUMMARY OF THE INVENTION

In a general aspect, the present invention provides mutant lysins, mutated so as to have the capacity to readily dimerize, thereby generating dimeric lysins having enhanced activity or bacterial killing activity, and greater stability, including for longer term stability in an animal or mammal and longer acting bacterial killing capability in a clinically- or biologically-relevant setting.

In one aspect, the present invention provides for isolated dimeric anti-bacterial phage lysins comprising two phage lysin monomers specific for bacteria covalently linked to each other, wherein said dimer has killing activity against one or more specific bacteria. In one aspect, the present invention provides for isolated dimeric *Streptococcus*-specific phage lysins comprising two *Streptococcus*-specific phage lysin monomers covalently linked to each other, wherein said dimer has killing activity against one or more *Streptococcus* bacteria. In certain embodiments, the lysin monomers have at least 80%, at least 90%, at least 95% amino acid sequence identity to the unmutated Cpl-1 lysin as set out in FIGS. 1 and 6 and SEQ ID NO: 1. In certain embodiments, the lysin monomers have at least 80%, at least 90%, at least 95% amino acid sequence identity to the unmutated Pal lysin as set out in FIG. 7 and SEQ ID NO: 5.

In certain embodiments, the lysin monomers are chemically cross-linked to each other. In one such instance the monomers may be chemically crosslinked via reactive groups or via amino acids in the monomer sequence, including modified, altered or mutant amino acids. The lysin monomers may be covalently linked to each other by a disulfide bond. In certain exemplary embodiments, each lysin monomer has a Cys residue located in close proximity to the C-terminus, particularly between 14 and 20 amino acids from the C-terminus. In certain embodiments, the lysin monomers do not have a Cys residue in the first 45 residues. Exemplary mutant Cpl-1 lysins are provided herein, including in FIG. 6 and in Table 1. In one particular embodiment, the lysin monomers have an amino acid sequence as set out in FIG. 6 or provided in Table 1. In another embodiment, the lysin monomers have an amino acid sequence as set out in FIG. 7. In certain embodiments, the lysin monomers comprise a catalytic domain of a first *Streptococcus*-specific phage lysin and a binding domain of a second *Streptococcus*-specific phage lysin.

The present invention provides for methods of treating a mammal suffering from a disease or condition caused by a streptococcal infection by administering a composition comprising a therapeutically effective amount of a dimeric lysin comprising two *Streptococcus*-specific phage lysin monomers covalently linked to each other, wherein said dimer has killing activity against one or more *Streptococcus* bacteria. In certain embodiments, the infection is caused by *Streptococcus pneumoniae*. The disease or condition caused by the *Streptococcus pneumoniae* infection may be at least one of bacteremia, meningitis, pneumonia, otitis media, or sinusitis.

The present invention provides for methods of inhibiting or decolonizing a streptococcal infection in a mammal by administering a composition comprising a therapeutically effective amount of a dimeric lysin comprising two *Streptococcus*-specific phage lysin monomers covalently linked to each other, wherein said dimer has killing activity against one or more *Streptococcus* bacteria. In certain embodiments, the infection is caused by *Streptococcus pneumoniae*. The disease or condition caused by the *Streptococcus pneumoniae* infection may be at least one of bacteremia, meningitis, pneumonia, otitis media, or sinusitis.

In an aspect of the invention, a method is provided of killing gram-positive bacteria comprising the step of contacting the bacteria with a composition comprising an amount of a mutant dimeric lysin polypeptide effective to kill gram-positive bacteria, wherein a monomeric lysin is modified or altered so as to be a dimeric lysin polypeptide comprising two antibacterial phage lysin monomers covalently linked to each other and effective to kill gram-positive bacteria. In a particular such aspect, a method is provided for killing *Streptococcus* bacteria comprising the step of contacting the bacteria with a composition comprising an amount of a mutant dimeric lysin polypeptide effective to kill *Streptococcus* bacteria, wherein a monomeric *Streptococcus* lysin is modified or altered so as to be a dimeric lysin polypeptide comprising two *Streptococcus* phage lysin monomers covalently linked to each other and effective to kill *Streptococcus* bacteria.

Thus, a method is provided of killing *Streptococcus* bacteria comprising the step of contacting the bacteria with a composition comprising an amount of an isolated dimeric *Streptococcus* Cpl-1 lysin polypeptide effective to kill the *Streptococcus* bacteria, the isolated lysin polypeptide comprising a mutant Cpl-1 lysin comprising two Cpl-1 lysin monomers covalently linked to each other. In a particular aspect, a method is provided of killing *Streptococcus* bacteria comprising the step of contacting the bacteria with a composition comprising an amount of an isolated lysin polypeptide effective to kill the *Streptococcus* bacteria, the isolated lysin polypeptide comprising the amino acid sequence of SEQ ID NO: 3 or variants thereof having at least 80% homology, 85% homology, 90% homology or 95% homology to the polypeptide of SEQ ID NO: 3 and effective to kill the gram-positive bacteria.

A method is further provided of killing *Streptococcus* bacteria comprising the step of contacting the bacteria with a composition comprising an amount of an isolated dimeric *Streptococcus* Pal lysin polypeptide effective to kill the *Streptococcus* bacteria, the isolated lysin polypeptide comprising a mutant Pal lysin comprising two Pal lysin monomers covalently linked to each other. In a particular aspect, a method is provided of killing *Streptococcus* bacteria comprising the step of contacting the bacteria with a composition comprising an amount of an isolated lysin polypeptide effective to kill the *Streptococcus* bacteria, the isolated lysin polypeptide comprising the amino acid sequence of SEQ ID NO: 6 or variants thereof having at least 80% homology, 85% homology, 90% homology or 95% homology to the polypeptide of SEQ ID NO: 6 and effective to kill the gram-positive bacteria.

The invention provides pharmaceutical compositions comprising a therapeutically effective amount of a dimeric lysin comprising two *Streptococcus*-specific phage lysin monomers covalently linked to each other, wherein said dimer has killing activity against one or more *Streptococcus* bacteria, and a pharmaceutically acceptable carrier.

The invention provides pharmaceutical compositions comprising a therapeutically effective amount of a dimeric lysin comprising two *Streptococcus*-specific phage lysin monomers covalently linked to each other, wherein said dimer has killing activity against one or more *Streptococcus* bacteria and wherein said killing activity is greater than the killing activity of any one of the *Streptococcus*-specific phage lysin monomers, and a pharmaceutically acceptable carrier.

In an additional aspect, the present invention provides for anti-microbial compositions for sanitizing or decontaminating porous or non-porous surfaces comprising a dimeric lysin comprising two *Streptococcus*-specific phage lysin monomers covalently linked to each other, wherein said dimer has killing activity against one or more *Streptococcus* bacteria.

The compositions of the invention may particularly demonstrate or have killing activity against one or more *Streptococcus* bacteria strains, particularly selected from the group consisting of *Streptococcus suis, Streptococcus equi, Streptococcus agalactiae* (GBS), *Streptococcus pyogenes* (GAS), *Streptococcus sanguinis, Streptococcus gordonii, Streptococcus dysgalactiae, Streptococcus* GES and *Streptococcus pneumonia*.

The invention provides methods for decontaminating inanimate surfaces suspected of containing infectious bacteria comprising treatment of said surfaces with a bacteriocidally or bacteriostatically effective amount of an antimicrobial composition for sanitizing or decontaminating porous or non-porous surfaces comprising a dimeric lysin comprising two *Streptococcus*-specific phage lysin monomers covalently linked to each other, wherein said dimer has killing activity against one or more *Streptococcus* bacteria.

The present invention includes a dimeric protein comprising two *Streptococcus*-specific phage lysin binding domains covalently linked to each other. The invention provides a dimeric protein comprising two *Streptococcus*-specific phage lysin binding domains covalently linked to each other, wherein at least one of said phage lysin binding domain is further conjugated to a label. A label may be any molecule which produces, or can be induced to produce, a detectable signal. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The diagnostic utility of the present invention extends to the use of the present lysin polypeptides in assays to screen for the presence of gram-positive bacteria, to screen for the presence of susceptible gram-positive bacteria, or to determine the susceptibility of bacteria to killing or lysing by a one or more lysin polypeptide(s) of the invention.

Lysin polypeptides which are modified and are chimeric or fusion proteins, or which are labeled, are contemplated and provided herein. In a chimeric or fusion protein, the lysin polypeptide(s) of the invention may be covalently attached to an entity which may provide additional function or enhance the use or application of the lysin polypeptide(s), including for instance a tag, label, targeting moiety or ligand, a cell binding or cell recognizing motif or agent, an antibacterial agent, an antibody, an antibiotic. Exemplary labels include a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. The label may be an enzyme, and detection of the labeled lysin polypeptide may be accomplished by any of the presently utilized or accepted colorimetric, spectrophotometric, fluorospectrophotometric, amperometric or gasometric techniques known in the art.

Other objects and advantages will become apparent to those skilled in the art from a review of the following description which proceeds with reference to the following illustrative drawings.

BRIEF DESCRIPTION OF THE DRAWINGS

FIG. 1. ClustalW alignment of Cpl-1 (SEQ ID NO: 1) and *S. pneumoniae* LytA (SEQ ID NO: 2) amino-acid sequences. The two catalytic residues (D10 and E94) are in red. The 13 amino acids involved in natural dimerization of lytA and corresponding amino-acids in Cpl-1 are indicated by underlining. The residue D324 is indicated in blue.

FIG. 6 depicts aligned amino acid sequences of (unmutated) Cpl-1 (SEQ ID NO:1), and mutant lysins C45S (SEQ ID NO:4) and C45S,D324C (SEQ ID NO:3). Amino acid changes in the mutants are underlined.

FIG. 7 depicts aligned amino acid sequences of Cpl-1 (SEQ ID NO:1), Pal (SEQ ID NO: 5) and *S. pneumoniae* LytA (SEQ ID NO: 2) amino acid sequences. Identical amino acids among all three sequences are denoted by an asterisk *. The 13 amino acids involved in natural dimerization of LytA and analogous amino acids in Cpl-1 and in Pal are indicated by underlining and bold. The corresponding amino acids mutated in exemplary dimer mutants of Cpl-1 (residue D324) and Pal (residue D280) are boxed.

DETAILED DESCRIPTION

Figure 2A:
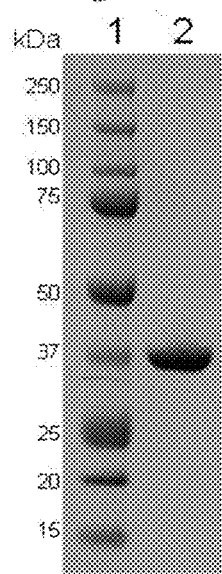
FIG. 2A-2C depicts (A) Coomassie stained non-reducing SDS-PAGE gel of the purified Cpl-1. Lane 1, molecular weight marker, and lane 2, purified Cpl-1 obtained by affinity purification on DEAE-Sepharose. (B) Coomassie stained non-reducing SDS-PAGE gel of the purified Cpl-$1^{C45S,D324C}$ mutant. Lane 1, molecular weight marker. Lane 2, purified Cpl-$1^{C45S,D324C}$ obtained by affinity purification on DEAE-sepharose, and lane 3, Cpl-$1^{C45S,D324C}$ reduced with 10mM of DTT. (C) Coomassie stained non-reducing SDS-PAGE gel of the purified Cpl-$1^{C45S,D324C}$ mutant dimer enrichment after gel filtration on Sephadex G100. Lane 1, molecular weight marker. Lane 2, purified Cpl-$1^{C45S,D324C}$ dimer obtained by gel filtration on Sephadex G100 (first purification), and lane 3, purified Cpl-$1^{C45S,D324C}$ dimer obtained by gel filtration on Sephadex G100 (second purification).

Dimeric *Streptococcus*-specific bacteriophage lysins with killing activity against *S. pneumoniae* are described herein. Typically, the dimeric phage lysins contain two *Streptococcus*-specific phage lysin monomers covalently linked to each other, wherein said dimer has activity against one or more *Streptococcus* bacteria. The lysin monomers of the lysin dimer may have at least 80%, 85%, 90%, 95%, 97%, 98%, 99%, or even at least 99.5% amino acid sequence identity with unmutated Cpl-1 (FIG. 1, SEQ ID NO: 1). The lysin monomers of the lysin dimer may have at least 80%, 85%, 90%, 95%, 97%, 98%, 99%, or even at least 99.5% amino acid sequence identity with unmutated Pal (FIG. 7, SEQ ID NO: 5). The stabilized dimeric lysin(s) provided herein demonstrate increased bacterial killing activity, approximately twice the in vitro anti-bacterial activity of the original monomeric molecule. The dineric lysin(s) also show decreased plasma clearance by a factor close to 10 between 5 minutes and 5 hours post-infection, with decreased plasma clearance or increased stability in plasma or in an animal.

FIG. 1 demonstrates that the amino acid sequences of the C-terminal regions of LytA and the *Streptococcus* lysin Cpl-1 are homologous (73/142 identical residues, and 55/69 residues are conservative substitutions). The C-terminal 13 amino-acids are responsible for the dimerization of the *Streptococcus pneumoniae* autolysin LytA. Interestingly, within this region 10/13 amino acids are identical between Cpl-1 and LytA. The fully active LytA is a choline-binding homodimer composed by the tail to tail association of two LytA monomers initiated by choline interaction. The principal driving force for dimerization is provided by a hydrophobic core resulting from inter-molecular hydrophobic interactions between several residues in the C-terminal choline binding regions 6 and 7 (8). The 13 C-terminal residues of LytA are responsible for the formation of the active homodimer, whose activity is significantly greater than the native monomer. In fact, a recombinant monomeric form of LytA lacking this 13 amino acid stretch (27) retains less than 10% of the enzyme's catalytic efficiency (24). Sequence alignment of Cpl-1 and LytA revealed extended similarities, especially within the C-terminal tail of the enzyme involved in LytA dimerization (FIG. 1). The existence of a glomerular filtration threshold estimated to be approximately 60-65 kDa in humans (17) suggests that the dimeric form of Cpl-1 (MW of 74 kDa) could show a significant decrease in systemic clearance compared to the monomer. A Cpl-1 dimer composed of two monomers covalently linked and stabilized by a disulfide bond has thus herein been engineered and examined its in vitro activity and in vivo plasma clearance compared to the monomeric form of Cpl-1. Moreover, and because several other phage lysins have been shown or are suspected to dimerize (25, 26), this represents a general way to increase the activity and/or pharmacokinetics of certain phage lysins.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions as provided and set out below and in this section.

The terms "*Streptococcus* dimer(ic) lysin(s)", "Cpl-1 dimeric lysin(s)", "Cpl-1 dimer(s)", "dimeric Cpl-1" and any variants not specifically listed, may be used herein interchangeably, and as used throughout the present application and claims refer to proteinaceous material including single or multiple proteins, and particularly dimer proteins, and extends to those proteins having the amino acid sequence data described herein and presented in FIG. 6 and in Table 1, and in SEQ ID NO: 3, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "*Streptococcus* dimer(ic) lysin(s)", "Cpl-1 dimeric lysin(s)", "Cpl-1 dimer(s)", "dimeric Cpl-1" are intended to include within their scope proteins specifically recited herein as well as all substantially homologous analogs, fragments or truncations, and allelic variations.

The terms "*Streptococcus* dimer(ic) lysin(s)", "Pal dimeric lysin(s)", "Pal dimer(s)", "dimeric Pal" and any variants not specifically listed, may be used herein interchangeably, and as used throughout the present application and claims refer to proteinaceous material including single or multiple proteins, and particularly dimer proteins, and extends to those proteins having the amino acid sequence data described herein and presented in FIG. 7, and in SEQ ID NO: 5, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "*Streptococcus* dimer(ic) lysin(s)", "Pal dimeric lysin(s)", "Pal dimer(s)", "dimeric Pal" are intended to include within their scope proteins specifically recited herein as well as all substantially homologous analogs, fragments or truncations, and allelic variations.

Polypeptides and Lytic Enzymes

A "lytic enzyme" includes any bacterial cell wall lytic enzyme that kills one or more bacteria under suitable conditions and during a relevant time period. Examples of lytic enzymes include, without limitation, various amidase cell wall lytic enzymes.

A "*Streptococcus* lytic enzyme" includes a lytic enzyme that is capable of killing at least one or more *Streptococcus* bacteria under suitable conditions and during a relevant time period.

A "bacteriophage lytic enzyme" refers to a lytic enzyme extracted or isolated from a bacteriophage or a synthesized lytic enzyme with a similar protein structure that maintains a lytic enzyme functionality.

A lytic enzyme is capable of specifically cleaving bonds that are present in the peptidoglycan of bacterial cells to disrupt the bacterial cell wall. It is also currently postulated that the bacterial cell wall peptidoglycan is highly conserved among most bacteria, and cleavage of only a few bonds to may disrupt the bacterial cell wall. The bacteriophage lytic enzyme may be an amidase, although other types of enzymes are possible. Examples of lytic enzymes that cleave these bonds are various amidases such as muramidases, glucosaminidases, endopeptidases, or N-acetyl-muramoyl-L-alanine amidases. Fischetti et al (2008) reported that the Cl streptococcal phage lysin enzyme was an amidase. Garcia et al (1987, 1990) reported that the Cpl lysin from a *S. pneumoniae* from a Cp-1 phage was a lysozyme. Caldentey and Bamford (1992) reported that a lytic enzyme from the phi 6 *Pseudomonas* phage was an endopeptidase, splitting the peptide bridge formed by melo-diaminopimilic acid and D-alanine. The *E. coli* T1 and T6 phage lytic enzymes are amidases as is the lytic enzyme from *Listeria* phage (ply)

(Loessner et al, 1996). There are also other lytic enzymes known in the art that are capable of cleaving a bacterial cell wall.

A "lytic enzyme genetically coded for by a bacteriophage" includes a polypeptide capable of killing a host bacteria, for instance by having at least some cell wall lytic activity against the host bacteria. The polypeptide may have a sequence that encompasses native sequence lytic enzyme and variants thereof. The polypeptide may be isolated from a variety of sources, such as from a bacteriophage ("phage"), or prepared by recombinant or synthetic methods, such as those described by Garcia et al and also as provided herein. The polypeptide may comprise a choline binding portion at the carboxyl terminal side and may be characterized by an enzyme activity capable of cleaving cell wall peptidoglycan (such as amidase activity to act on amide bonds in the peptidoglycan) at the amino terminal side. Lytic enzymes have been described which include multiple enzyme activities, for example two enzymatic domains, such as PlyGBS lysin. Generally speaking, a lytic enzyme may be between 25,000 and 35,000 daltons in molecular weight and comprise a single polypeptide chain; however, this can vary depending on the enzyme chain. The molecular weight most conveniently can be determined by assay on denaturing sodium dodecyl sulfate gel electrophoresis and comparison with molecular weight markers.

"A native sequence phage associated lytic enzyme" includes a polypeptide having the same amino acid sequence as an enzyme derived from a bacteria. Such native sequence enzyme can be isolated or can be produced by recombinant or synthetic means.

The term "native sequence enzyme" encompasses naturally occurring forms (e.g., alternatively spliced or altered forms) and naturally-occurring variants of the enzyme. In one embodiment of the invention, the native sequence enzyme is a mature or full-length polypeptide that is genetically coded for by a gene from a bacteriophage specific for *Streptococcus*, and particularly that of native Cpl-1 lysin or of native Pal lysin. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al, Proc. Natl. Acad. Sci. USA 85: 914-918 (1988); Garcia et al., Streptococcal Genetics (J. J. Ferretti and Curtis eds., 1987); Lopez et al., FEMS Microbiol. Lett. 100: 439-448 (1992); Romero et al., J. Bacteriol. 172: 5064-5070 (1990); Ronda et al., Eur. J. Biochem. 164: 621-624 (1987) and Sanchez et al., Gene 61: 13-19 (1987). The contents of each of these references, particularly the sequence listings and associated text that compares the sequences, including statements about sequence homologies, are specifically incorporated by reference in their entireties.

"A variant sequence lytic enzyme" includes a lytic enzyme characterized by a polypeptide sequence that is different from that of a lytic enzyme, but retains functional activity. The lytic enzyme can, in some embodiments, be genetically coded for by a bacteriophage specific for *Streptococcus* having a particular amino acid sequence identity with the lytic enzyme sequence(s) hereof, as provided in FIG. 1, FIG. 6 and FIG. 7, including the variant lytic enzymes of SEQ ID NO: 3, 4, and 5. For example, in some embodiments, a functionally active lytic enzyme can kill *Streptococcus* bacteria, and other susceptible bacteria as provided herein, or as previously described and known to the skilled artisan, by disrupting the cellular wall of the bacteria. An active lytic enzyme may have a 60, 65, 70, 75, 80, 85, 90, 95, 97, 98, 99 or 99.5% amino acid sequence identity with the lytic enzyme sequence(s) hereof, as provided in FIG. 1, FIG. 6 and FIG. 7, including the variant lytic enzymes of SEQ ID NO: 3, 4, and 5. Such phage associated lytic enzyme variants include, for instance, lytic enzyme polypeptides wherein one or more amino acid residues are changed or are added or deleted, including at the N or C terminus of the sequence of the lytic enzyme sequence(s) hereof. In a particular aspect, a phage associated lytic enzyme will have at least about 80% or 85% amino acid sequence identity with native phage associated lytic enzyme sequences, particularly at least about 90% (e.g. 90%) amino acid sequence identity. Most particularly a phage associated dimeric lytic enzyme variant will have at least about 95% (e.g. 95%) amino acid sequence identity with the native phage associated the lytic enzyme sequence(s) hereof, as provided in FIG. 1, FIG. 6 and FIG. 7 or in Table 1 or the sequences hereof including SEQ ID NO: 1 or 5, or the mutant sequences of SEQ ID NO: 3,4, or 6.

"Percent amino acid sequence identity" with respect to the phage associated lytic enzyme sequences identified is defined herein as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity.

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity.

To determine the percent identity of two nucleotide or amino acid sequences, the sequences are aligned for optimal comparison purposes (e.g., gaps may be introduced in the sequence of a first nucleotide sequence). The nucleotides or amino acids at corresponding nucleotide or amino acid positions are then compared. When a position in the first sequence is occupied by the same nucleotide or amino acid as the corresponding position in the second sequence, then the molecules are identical at that position. The percent identity between the two sequences is a function of the number of identical positions shared by the sequences (i.e., % identity=# of identical positions/total # of positions.times.100).

The determination of percent identity between two sequences may be accomplished using a mathematical algorithm. A preferred, non-limiting example of a mathematical algorithm utilized for the comparison of two sequences is the algorithm of Karlin et al., Proc. Natl. Acad. Sci. USA, 90:5873-5877 (1993). Such an algorithm is incorporated into the NBLAST program which may be used to identify sequences having the desired identity to nucleotide sequences of the invention. To obtain gapped alignments for comparison purposes, Gapped BLAST may be utilized as described in Altschul et al., Nucleic Acids Res, 25:3389-3402 (1997). When utilizing BLAST and Gapped BLAST programs, the default parameters of the respective programs (e.g., NBLAST) may be used. See the programs provided by National Center for Biotechnology Information, National Library of Medicine, National Institutes of Health. In one embodiment, parameters for sequence comparison may be set at W=12. Parameters may also be varied (e.g., W=5 or W=20). The value "W" determines how many continuous nucleotides must be identical for the program to identify two sequences as containing regions of identity.

"Polypeptide" includes a polymer molecule comprised of multiple amino acids joined in a linear manner A polypeptide can, in some embodiments, correspond to molecules encoded by a polynucleotide sequence which is naturally occurring. The polypeptide may include conservative substitutions where the naturally occurring amino acid is replaced by one having similar properties, where such conservative substitutions do not alter the function of the polypeptide (see, for example, Lewin "Genes V" Oxford University Press Chapter 1, pp. 9-13 1994).

The term "altered lytic enzymes" includes shuffled and/or chimeric lytic enzymes.

Phage lytic enzymes specific for bacteria infected with a specific phage have been found to effectively and efficiently break down the cell wall of the bacterium in question. The lytic enzyme is believed to lack proteolytic enzymatic activity and is therefore non-destructive to mammalian proteins and tissues when present during the digestion of the bacterial cell wall. As shown by Loeffler et al, "Rapid Killing of *Streptococcus pneumoniae* with a Bacteriophage Cell Wall Hydrolase," Science, 294: 2170-2172 (Dec. 7, 2001), and supplemental material thereto published online by Science magazine, which are incorporated herein by reference in their entirety, a purified pneumococcal bacteriophage lytic enzyme, such as Pal, is able to kill various pneumococci. Loeffler et al. have shown through these experiments that within seconds after contact, the lytic enzyme Pal is able to kill 15 clinical stains of *S. pneumoniae*, including the most frequently isolated serogroups and penicillin resistant stains, in vitro. Treatment of mice with Pal was also able to eliminate or significantly reduce nasal carriage of serotype 14 in a dose-dependent manner. Furthermore, because it has been found that the action of Pal, like other phage lytic enzymes, but unlike antibiotics, was rather specific for the target pathogen, it is likely that the normal flora will remain essentially intact (M. J. Loessner, G. Wendlinger, S. Scherer, Mol Microbiol 16, 1231-41. (1995) incorporated herein by reference). As demonstrated herein, for example, the mutant Cpl-1 lysin, particularly the dimeric lysin, dimeric Cpl-1 lysin, is effective in killing *Streptococcus* strains, including *Streptococcus pneumonia*.

A lytic enzyme or polypeptide of the invention may be produced by the bacterial organism after being infected with a particular bacteriophage as either a prophylactic treatment for preventing those who have been exposed to others who have the symptoms of an infection from getting sick, or as a therapeutic treatment for those who have already become ill from the infection. In as much the lysin polypeptide sequences and nucleic acids encoding the lysin polypeptides are provided herein, the lytic enzyme(s)/polypeptide(s) may be preferably produced via the isolated gene for the lytic enzyme from the phage genome, putting the gene into a transfer vector, and cloning said transfer vector into an expression system, using standard methods of the art, including as exemplified herein. The lytic enzyme(s) or polypeptide(s) may be truncated, chimeric, shuffled or "natural," and may be in combination. Relevant U.S. Pat. No. 5,604,109 is incorporated herein in its entirety by reference. An "altered" lytic enzyme can be produced in a number of ways. In a preferred embodiment, a gene for the altered lytic enzyme from the phage genome is put into a transfer or movable vector, preferably a plasmid, and the plasmid is cloned into an expression vector or expression system. The expression vector for producing a lysin polypeptide or enzyme of the invention may be suitable for *E. coli, Bacillus*, or a number of other suitable bacteria. The vector system may also be a cell free expression system. All of these methods of expressing a gene or set of genes are known in the art. The lytic enzyme may also be created by infecting *Streptococcus* with a bacteriophage specific for *Streptococcus*, wherein said at least one lytic enzyme exclusively lyses the cell wall of said *Streptococcus* having at most minimal effects on other, for example natural or commensal, bacterial flora present.

A "chimeric protein" or "fusion protein" comprises all or (preferably a biologically active portion or domain) part of a polypeptide of the invention operably linked to a heterologous polypeptide. Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides also may be used to treat a bacterial infection by cleaving the cell wall in more than one location, thus potentially providing more rapid or effective (or synergistic) killing from a single lysin molecule or chimeric peptide.

A "heterologous" region of a DNA construct or peptide construct is an identifiable segment of DNA within a larger DNA molecule or peptide within a larger peptide molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA or peptide as defined herein.

The term "operably linked" means that the polypeptide of the disclosure and the heterologous polypeptide are fused in-frame. The heterologous polypeptide can be fused to the N-terminus or C-terminus of the polypeptide of the disclosure. Chimeric proteins are produced enzymatically by chemical synthesis, or by recombinant DNA technology. A number of chimeric lytic enzymes have been produced and studied. Gene E-L, a chimeric lysis constructed from bacteriophages phi XI74 and MS2 lysis proteins E and L, respectively, was subjected to internal deletions to create a series of new E-L clones with altered lysis or killing properties. The lytic activities of the parental genes E, L, E-L, and the internal truncated forms of E-L were investigated in this study to characterize the different lysis mechanism, based on differences in the architecture of the different membranes spanning domains. Electron microscopy and release of marker enzymes for the cytoplasmic and periplasmic spaces revealed that two different lysis mechanisms can be distinguished depending on penetration of the proteins of either the inner membrane or the inner and outer membranes of the *E. coli* (FEMS Microbiol. Lett. (1998) 164(1): 159-67 (incorporated herein by reference). One example of a useful fusion protein is a GST fusion protein in which the polypeptide of the disclosure is fused to the C-terminus of a GST sequence. Such a chimeric protein can facilitate the purification of a recombinant polypeptide of the disclosure.

In another embodiment, the chimeric protein or peptide contains a heterologous signal sequence at its N-terminus. For example, the native signal sequence of a polypeptide of the disclosure can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992, incorporated herein by reference). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

The fusion protein may combine a lysin polypeptide with a protein or polypeptide having a different capability, or providing an additional capability or added character to the lysin polypeptide. The fusion protein may be an immunoglobulin fusion protein in which all or part of a polypeptide of the disclosure is fused to sequences derived from a member of the immunoglobulin protein family. The immunoglobulin may be an antibody, for example an antibody directed to a surface protein or epitope of a susceptible or target bacteria. An immunoglobulin fusion protein can be incorporated into a pharmaceutical composition and administered to a subject to inhibit an interaction between a ligand (soluble or membrane-bound) and a protein on the surface of a cell (receptor), to thereby suppress signal transduction in vivo. The immunoglobulin fusion protein can alter bioavailability of a cognate ligand of a polypeptide of the disclosure. Inhibition of ligand/receptor interaction may be useful therapeutically, both for treating bacterial-associated diseases and disorders for modulating (i.e. promoting or inhibiting) cell survival. Moreover, an immunoglobulin fusion protein of the disclosure can be used as an immunogen to produce antibodies directed against a polypeptide of the disclosure in a subject, to purify ligands and in screening assays to identify molecules which inhibit the interaction of receptors with ligands. Chimeric and fusion proteins and peptides of the disclosure can be produced by standard recombinant DNA techniques.

The fusion gene can be synthesized by conventional techniques, including automated DNA synthesizers. Alternatively, PCR amplification of gene fragments can be carried out using anchor primers which give rise to complementary overhangs between two consecutive gene fragments which subsequently can be annealed and reamplified to generate a chimeric gene sequence (see, i.e., Ausubel et al., supra). Moreover, many expression vectors are commercially available that already encode a fusion moiety (i.e., a GST polypeptide). A nucleic acid encoding a polypeptide of the invention can be cloned into such an expression vector such that the fusion moiety is linked in-frame to the polypeptide of the invention.

As used herein, shuffled proteins or peptides, gene products, or peptides for more than one related phage protein or protein peptide fragments have been randomly cleaved and reassembled into a more active or specific protein. Shuffled oligonucleotides, peptides or peptide fragment molecules are selected or screened to identify a molecule having a desired functional property. This method is described, for example, in Stemmer, U.S. Pat. No. 6,132,970. (Method of shuffling polynucleotides); Kauffman, U.S. Pat. No. 5,976,862 (Evolution via Condon-based Synthesis) and Huse, U.S. Pat. No. 5,808,022 (Direct Codon Synthesis). The contents of these patents are incorporated herein by reference. Shuffling can be used to create a protein that is more active, for instance up to 10 to 100 fold more active than the template protein. The template protein is selected among different varieties of lysin proteins. The shuffled protein or peptides constitute, for example, one or more binding domains and one or more catalytic domains. Each binding or catalytic domain is derived from the same or a different phage or phage protein. The shuffled domains are either oligonucleotide based molecules, as gene or gene products, that either alone or in combination with other genes or gene products are translatable into a peptide fragment, or they are peptide based molecules. Gene fragments include any molecules of DNA, RNA, DNA-RNA hybrid, antisense RNA, Ribozymes, ESTs, SNIPs and other oligonucleotide-based molecules that either alone or in combination with other molecules produce an oligonucleotide molecule capable or incapable of translation into a peptide.

The dimeric form(s) of the lysin protein or peptides and peptide fragments, as disclosed herein, includes protein or peptides and peptide fragments that are chemically synthesized or prepared by recombinant DNA techniques, or both. These techniques include, for example, chimerization and shuffling. When the protein or peptide is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

A signal sequence of a polypeptide can facilitate transmembrane movement of the protein and peptides and peptide fragments of the disclosure to and from mucous membranes, as well as by facilitating secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the disclosure can pertain to the described polypeptides having a signal sequence, as well as to the signal sequence itself and to the polypeptide in the absence of the signal sequence (i.e., the cleavage products). A nucleic acid sequence encoding a signal sequence of the disclosure can be operably linked in an expression vector to a protein of interest, such as a protein which is ordinarily not secreted or is otherwise difficult to isolate. The signal sequence directs secretion of the protein, such as from an eukaryotic host into which the expression vector is transformed, and the signal sequence is subsequently or concurrently cleaved. The protein can then be readily purified from the extracellular medium by art recognized methods. Alternatively, the signal sequence can be linked to a protein of interest using a sequence which facilitates purification, such as with a GST domain.

The present invention also pertains to other variants of the polypeptides of the invention. Such variants may have an altered amino acid sequence which can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of the disclosure which function as either agonists (mimetics) or as antagonists can be identified by screening combinatorial libraries of mutants, i.e., truncation mutants, of the protein of the disclosure for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (i.e., for phage display). There are a variety of methods which can be used to produce libraries of potential variants of the polypeptides of the disclosure from a degenerate oligonucleotide sequence. Methods for synthesizing degenerate oligonucleotides are known in the art (see, i.e., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477, all herein incorporated by reference).

In addition, libraries of fragments of the coding sequence of a polypeptide of the disclosure can be used to generate a variegated population of polypeptides for screening and subsequent selection of variants, active fragments or truncations. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal and internal fragments of various sizes of the protein of interest. Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the disclosure (Arkin and Yourvan (1992) Proc. Natl. Acad. Sci. USA 89:7811-7815; Delgrave et al. (1993) Protein Engineering 6(3):327-331) immunologically active portions of a protein or peptide fragment include regions that bind to antibodies that recognize the phage enzyme. In this context, the smallest portion of a protein (or nucleic acid that encodes the protein) according to embodiments is an epitope that is recognizable as specific for the phage that makes the lysin protein. Accordingly, the smallest polypeptide (and associated nucleic acid that encodes the polypeptide) that can be expected to bind antibody and is useful for some embodiments may be 8, 9, 10, 11, 12, 13, 15, 20, 25, 30, 35, 40, 45, 50, 55, 60, 65, 75, 85, or 100 amino acids long. Although small sequences as short as 8, 9, 10, 11, 12 or 15 amino acids long reliably comprise enough structure to act as epitopes, shorter sequences of 5, 6, or 7 amino acids long can exhibit epitopic structure in some conditions and have value in an embodiment.

Biologically active portions of a protein or peptide fragment of the embodiments, as described herein, include polypeptides comprising amino acid sequences sufficiently identical to or derived from the amino acid sequence of the phage protein of the disclosure, which include fewer amino acids than the full length protein of the phage protein and exhibit at least one activity of the corresponding full-length protein. Typically, biologically active portions comprise a domain or motif with at least one activity of the corresponding protein. A biologically active portion of a protein or protein fragment of the disclosure can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide of the embodiments.

Homologous proteins and nucleic acids can be prepared that share functionality with such small proteins and/or nucleic acids (or protein and/or nucleic acid regions of larger molecules) as will be appreciated by a skilled artisan. Such small molecules and short regions of larger molecules that may be homologous specifically are intended as embodiments. Preferably the homology of such valuable regions is at least 50%, 65%, 75%, 80%, 85%, and preferably at least 90%, 95%, 97%, 98%, or at least 99% compared to the lysin polypeptides provided herein, including as set out in FIGS. 1 and 6. These percent homology values do not include alterations due to conservative amino acid substitutions.

Two amino acid sequences are "substantially homologous" when at least about 70% of the amino acid residues (preferably at least about 80%, at least about 85%, and preferably at least about 90 or 95%) are identical, or represent conservative substitutions. The sequences of comparable lysins, such as comparable Cpl-1 lysins, or comparable *Streptococcus* lysins, are substantially homologous when one or more, or several, or up to 10%, or up to 15%, or up to 20% of the amino acids of the lysin polypeptide are substituted with a similar or conservative amino acid substitution, and wherein the comparable lysins have the profile of activities, anti-bacterial effects, and/or bacterial specificities of a lysin, such as the Cpl-1 lysins, disclosed herein.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Mutations can be made in the amino acid sequences, or in the nucleic acid sequences encoding the polypeptides and lysins herein, including in the lysin sequences set out in FIG. 1, FIG. 6 or in FIG. 7, in SEQ ID NO: 1 or 5, or in active fragments or truncations thereof, such that a particular codon is changed to a codon which codes for a different amino acid, an amino acid is substituted for another amino acid, or one or more amino acids are deleted. Such a mutation is generally made by making the fewest amino acid or nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)

Another grouping may be those amino acids with phenyl groups: Phenylalanine, Tryptophan, Tyrosine Another grouping may be according to molecular weight (i.e., size of R groups):

| Glycine | 75 | Alanine | 89 |
|---|---|---|---|
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces .β-turns in the protein's structure.

A polypeptide or epitope as described herein may be used to generate an antibody and also can be used to detect binding to the lysin or to molecules that recognize the lysin protein. Another embodiment is a molecule such as an antibody or other specific binder that may be created through use of an epitope such as by regular immunization or by a phase display approach where an epitope can be used to screen a library if potential binders. Such molecules recognize one or more epitopes of lysin protein or a nucleic acid that encodes lysin protein. An antibody that recognizes an epitope may be a monoclonal antibody, a humanized antibody, or a portion of an antibody protein. Desirably the molecule that recognizes an epitope has a specific binding for that epitope which is at least 10 times as strong as the molecule has for serum albumin. Specific binding can be measured as affinity (Km). More desirably the specific binding is at least $10^2$, $10^3$, $10^4$, $10^5$, $10^6$, $10^7$, $10^8$, or even higher than that for serum albumin under the same conditions.

In a desirable embodiment the antibody or antibody fragment is in a form useful for detecting the presence of the lysin protein or, alternatively detecting the presence of a bacteria susceptible to the lysin protein. In a further embodiment the antibody may be attached or otherwise associated with the lysin polypeptide of the invention, for example in a chimeric or fusion protein, and may serve to direct the lysin to a bacterial cell or strain of interest or target. Alternatively, the lysin polypeptide may serve to direct the antibody or act in conjunction with the antibody, for example in lysing the bacterial cell wall fully or partially, so that the antibody may specifically bind to its epitope at the surface or under the surface on or in the bacteria. For example, a lysin of the invention may be attached to an anti-Streptococcal antibody and direct the antibody to its epitope.

A variety of forms and methods for antibody synthesis are known as will be appreciated by a skilled artisan. The antibody may be conjugated (covalently complexed) with a reporter molecule or atom such as a fluor, an enzyme that creates an optical signal, a chemilumiphore, a microparticle, or a radioactive atom. The antibody or antibody fragment may be synthesized in vivo, after immunization of an animal, for example, the antibody or antibody fragment may be synthesized via cell culture after genetic recombination. The antibody or antibody fragment may be prepared by a combination of cell synthesis and chemical modification.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CHI) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CHI domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0 120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "specific" may be used to refer to the situation in which one member of a specific binding pair will not show significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of refers to a product, particularly a peptide sequence, of a defined number of residues which is not covalently attached to a larger product. In the case of the peptide of the invention hereof, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which the lysin polypeptide(s) of the invention, or nucleic acid encoding such polypeptides will be, in accordance with the present invention. Polypeptides and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Polypeptides and nucleic acid may be formulated with diluents or adjuvants and still for practical purposes be isolated—for example the polypeptides will normally be mixed with polymers or mucoadhesives or other carriers, or will be mixed with pharmaceutically acceptable carriers or diluents, when used in diagnosis or therapy.

The dimeric lysin monomers of the invention may be chemically cross-linked together by a covalent bond, including in particular a covalent bond or other association such as between amino acids located between about 14 and 20 amino acids from the C-terminus of Cpl-1 lysin polypeptide (FIG. 1 and SEQ ID NO:1) or of Pal lysin (FIG. 7 and SEQ ID NO:5). The monomers may be cross-linked using chemical cross-linking agents. For example, a first monomer may be cross-linked to a second monomer between two cysteine residues. Example of cysteine-reactive cross-linking reagents include reagents such as 1,6-bismaleimidohexane (BMH), 1,3-dibromo-2-propanol (DBP), and mustard gas (bis(2-chloroethyl)sulfide; mustard). Alternative or other cross-linking reagents are known and may include N-hydroxysuccinamide (NHS) that link amine to amine, maleimides and pyridyldithiols that link sulfhydryls to sulfhydryls. Each could incorporate spacers to increase space and flexibility. The lysin monomers may be covalently associated or cross-linked via a linker peptide fused to their C-terminal ends or regions. Any art means for dimerizing may be utilized, provided that the C-terminal choline binding function and the N-terminal enzymatic function of the lysin is maintained.

The lysin monomers may be linked together by disulfide bonds between two cysteine residues. In certain embodiments the monomers are cross-linked together by a disulfide bond between two Cys residues located between 14 and 20 amino acids from the C-terminus of Cpl-1 or of Pal. The cross-linked cysteine residues may be at the same position on the lysin monomer polypeptide chains. In certain cases, cysteine residues in the first 45 residues of a lysin may not be present. An example of a lysin monomer which is cross-linked by Cys residues at position 324 is Cpl-1$^{C45S,}$ $^{D324C}$ (SEQ ID NO: 3). An example of a lysin monomer which is cross-linked by Cys residues at position 280 is Pal$^{D280C}$ (SEQ ID NO: 6).

Typically, lysins have two distinct functional domains consisting of a catalytic domain for peptidoglycan hydrolysis and a binding domain for recognition of surface moieties on the bacterial cell walls. The catalytic domains are relatively conserved among lysins. Thus, a dimeric lysin may be a chimeric in nature and comprise a dimer of lysin monomers which comprise a catalytic domain of a first *Streptococcus pneumoniae*-specific phage lysin and a binding domain of a second *Streptococcus*-specific phage lysin. In certain embodiments the catalytic domain of a first *Streptococcus*-specific phage lysin is from Cpl-1 or other *Streptococcus pneumoniae* phage lysin catalytic domains. In other embodiments, the binding domain of a second *Streptococcus pneumoniae*-specific phage lysin is from Cpl-1 or other *Streptococcus pneumoniae* phage lysin binding domains. Examples of a catalytic domain include amino acids 1-190 of Cpl-1. In other certain embodiments the catalytic domain of a first *Streptococcus*-specific phage lysin is from Pal or other *Streptococcus pneumoniae* phage lysin catalytic domains. In other embodiments, the binding domain of a second *Streptococcus pneumoniae*-specific phage lysin is from Pal or other *Streptococcus pneumoniae* phage lysin binding domains. Other examples of catalytic domains are the N-terminal half of the ClyS lysin and the PlyG lysin among others. Examples of binding domains include amino acids 191-326 of Cpl-1. Examples of binding domains include amino acids 155-296 of Pal. Other examples of binding domains are the C-terminal half of the ClyS and PlyG lysins among others. Those in the art could easily determine the exact amino acids that encompass these domains from sequence analysis and sequence alignments.

The dimeric lysins exhibit killing activity against one or more streptococcal bacteria such as *Streptococcus pneumoniae*. Killing activity may be determined using a killing assay such as that described in the example section below.

Nucleic Acids

Nucleic acids capable of encoding the dimeric lysin polypeptide(s) of the invention constitute an aspect of the invention. Representative nucleic acid sequences in this context are polynucleotide sequences coding for the dimeric polypeptide monomers of any of FIGS. 1, 6 and 7 and Table 1, SEQ ID NOs: 3 or 6, and sequences that hybridize, under stringent conditions, with complementary sequences of the nucleic acid sequence(s). Further variants of these sequences and sequences of nucleic acids that hybridize with those shown in the figures also are contemplated for use in production of lysing enzymes according to the disclosure, including natural variants that may be obtained. A large variety of isolated nucleic acid sequences or cDNA sequences that encode phage associated lysing enzymes and partial sequences that hybridize with such gene sequences are useful for recombinant production of the lysin enzyme(s) or polyp eptide(s) of the invention.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease SI), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Many of the herein contemplated variant DNA molecules include those created by standard DNA mutagenesis techniques, such as M13 primer mutagenesis. Details of these techniques are provided in Sambrook et al. (1989) In Molecular Cloning: A Laboratory Manual, Cold Spring Harbor, N.Y. (incorporated herein by reference). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the lysin polypeptide(s) are contemplated by the disclosure. Also included are small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage of *Streptococcus* and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above may also be defined as DNA sequences which hybridize under stringent conditions to the DNA sequences disclosed, or fragments thereof.

Hybridization conditions corresponding to particular degrees of stringency vary depending upon the nature of the hybridization method of choice and the composition and length of the hybridizing DNA used. Generally, the temperature of hybridization and the ionic strength (especially the sodium ion concentration) of the hybridization buffer will determine the stringency of hybridization. Calculations regarding hybridization conditions required for attaining particular degrees of stringency are discussed by Sambrook et al. (1989), In Molecular Cloning: A Laboratory Manual, Cold Spring Harbor, N.Y., chapters 9 and 11 (herein incorporated by reference).

An example of such calculation is as follows. A hybridization experiment may be performed by hybridization of a DNA molecule (for example, a natural variation of the lytic enzyme genetically coded for by a bacteriophage specific for *Bacillus anthracis*) to a target DNA molecule. A target DNA may be, for example, the corresponding cDNA which has been electrophoresed in an agarose gel and transferred to a nitrocellulose membrane by Southern blotting (Southern (1975). J. Mol. Biol. 98:503), a technique well known in the art and described in Sambrook et al. (1989) In Molecular Cloning: A Laboratory Manual, Cold Spring Harbor, N.Y. (incorporated herein by reference). Hybridization with a target probe labeled with isotopic $P^{32}$ labeled-dCTP is carried out in a solution of high ionic strength such as 6 times SSC at a temperature that is 20-25 degrees Celsius below the melting temperature, Tm (described infra). For such Southern hybridization experiments where the target DNA molecule on the Southern blot contains 10 ng of DNA or more, hybridization is carried out for 6-8 hours using 1-2 ng/ml radiolabeled probe (of specific activity equal to 109 CPM/mug or greater). Following hybridization, the nitrocellulose filter is washed to remove background hybridization. The washing conditions are as stringent as possible to remove background hybridization while retaining a specific hybridization signal. The term "Tm" represents the temperature above which, under the prevailing ionic conditions, the radiolabeled probe molecule will not hybridize to its target DNA molecule. The Tm of such a hybrid molecule may be estimated from the following equation: $T_m$=81.5° C.−16.6 (log lO of sodium ion concentration)+0.41(% G+C)−0.63(% formamide)−(600/1) where 1=the length of the hybrid in base pairs. This equation is valid for concentrations of sodium ion in the range of 0.01M to 0.4M, and it is less accurate for calculations of Tm in solutions of higher sodium ion concentration (Bolton and McCarthy (1962) Proc. Natl. Acad. Sci. USA 48:1390) (incorporated herein by reference). The equation also is valid for DNA having G+C contents within 30% to 75%, and also applies to hybrids greater than 100 nucleotides in length. The behavior of oligonucleotide probes is described in detail in Ch. 11 of Sambrook et al. (1989), In Molecular Cloning: A Laboratory Manual, Cold Spring Harbor, N.Y. (incorporated herein by reference). The preferred exemplified conditions described here are particularly contemplated for use in selecting variations of the lytic gene.

In preferred embodiments of the present disclosure, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. Preferably, stringent conditions are those under which DNA sequences with more than 6% mismatch will not hybridize.

The degeneracy of the genetic code further widens the scope of the embodiments as it enables major variations in the nucleotide sequence of a DNA molecule while maintaining the amino acid sequence of the encoded protein. For example, a representative amino acid residue is alanine. This may be encoded in the cDNA by the nucleotide codon triplet GCT. Because of the degeneracy of the genetic code, three other nucleotide codon triplets—GCT, GCC and GCA—also code for alanine. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this disclosure. Thus, it should be appreciated that also within the scope of the present invention are DNA sequences encoding a lysin of the present invention, including dimeric Cpl-1 and/or Pal lysins, which sequences code for a polypeptide having the same amino acid sequence as provided herein and in the Figures and Table 1, but which are degenerate thereto. By "degenerate to" is meant that a different three-letter codon is used to specify a particular amino acid.

While the site for introducing an amino acid sequence variation is predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure (EP 75,444A).

Substitutional variants are those in which at least one residue in the amino acid sequence has been removed and a different residue inserted in its place. Such substitutions may be made so as to generate no significant effect on the protein characteristics or when it is desired to finely modulate the characteristics of the protein. Amino acids which may be substituted for an original amino acid in a protein and which are regarded as conservative substitutions are described above and will be recognized by one of skill in the art.

Substantial changes in function or immunological identity may be made by selecting substitutions that are less conservative, for example by selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives or variants of the lytic polypeptide(s) by analyzing the ability of the derivative or variant proteins to lyse or kill susceptible bacteria, or to complement the sensitivity to DNA cross-linking agents exhibited by phages in infected bacteria hosts. These assays may be performed by transfecting DNA molecules encoding the derivative or variant proteins into the bacteria as described above or by incubating bacteria with expressed proteins from hosts transfected with the DNA molecules encoding the derivative or variant proteins.

While the site for introducing an amino acid sequence variation can be predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Another feature of this invention is the expression of the DNA sequences encoding dimeric lysins hereof. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids colE1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2□ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences~sequences that control the expression of a DNA sequence operatively linked to it~may be used in these vectors to express the DNA sequences of this invention. Such useful expression control sequences include, for example, the early or late promoters of SV40, CMV, vaccinia, polyoma or adenovirus, the lac system, the tip system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention.

Libraries of fragments of the coding sequence of a polypeptide can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein (Arkin and Yourvan (1992) Proc. Natl. Acad. Sci. USA 89:7811-7815; Delgrave et al. (1993) Protein Engineering 6(3):327-331).

Compositions

Therapeutic or pharmaceutical compositions comprising the dimeric lytic enzyme(s)/polypeptide(s) of the invention are provided in accordance with the invention, as well as related methods of use and methods of manufacture. Therapeutic or pharmaceutical compositions may comprise one or more dimeric lytic polypeptide(s), and optionally include truncated, chimeric or shuffled lytic enzymes, optionally combined with other components such as a carrier, vehicle, polypeptide, polynucleotide, holin protein(s), one or more antibiotics or suitable excipients, carriers or vehicles. The invention provides therapeutic compositions or pharmaceutical compositions of the lysins of the invention, including dimeric Cpl-1, and embodiment Cpl-1$^{C45S,D324C}$, for use in the killing, alleviation, decolonization, prophylaxis or treatment of gram-positive bacteria, including bacterial infections or related conditions. The invention provides therapeutic compositions or pharmaceutical compositions of the lysins of the invention, including dimeric Pal, and embodiment Pal$^{D280C}$, for use in the killing, alleviation, decolonization, prophylaxis or treatment of gram-positive bacteria, including bacterial infections or related conditions. Compositions comprising dimeric lysins, particularly dimeric Cpl-1, dimeric Pal, or combinations thereof, including truncations or variants thereof, are provided herein for use in the killing, alleviation, decolonization, prophylaxis or treatment of gram-positive bacteria, including bacterial infections or related conditions, particularly of *Streptococcus*.

The enzyme(s) or polypeptide(s) included in the therapeutic compositions may be one or more or any combination of phage associated dimeric lytic enzyme(s), truncated dimeric lytic polypeptides, variant dimeric lytic polypeptide(s), and chimeric and/or shuffled dimeric lytic enzymes. Additionally, different lytic polypeptide(s) genetically coded for by different phage for treatment of the same bacteria may be used. These lytic enzymes may also be any combination of "unaltered" dimeric lytic enzymes or polypeptides, truncated dimeric lytic polypeptide(s), variant dimeric lytic polypeptide(s), and chimeric and shuffled dimeric lytic enzymes. The dimeric lytic enzyme(s)/polypeptide(s) in a therapeutic or pharmaceutical composition for gram-positive bacteria, including *Streptococcus*, may be used alone or in combination with antibiotics or bacteriocidal or baceriostatic agents or, if there are other invasive bacterial organisms to be treated, in combination with other phage associated lytic enzymes specific for other bacteria being targeted. The lytic enzyme, truncated enzyme, variant enzyme, chimeric enzyme, and/or shuffled lytic enzyme may be used in conjunction with a holin protein. The amount of the holin protein may also be varied. Various antibiotics may be optionally included in the therapeutic composition with the enzyme(s) or polypeptide(s) and with or without the presence of lysostaphin. More than one lytic enzyme or polypeptide may be included in the therapeutic composition.

The pharmaceutical composition can also include one or more dimeric lytic enzymes, including isozymes, analogs, or variants thereof, produced by chemical synthesis or DNA recombinant techniques. In particular, altered lytic protein can be produced by amino acid substitution, deletion, truncation, chimerization, shuffling, or combinations thereof. The pharmaceutical composition may contain a combination of one or more dimeric lytic protein and one or more truncated, variant, chimeric or shuffled lytic protein. The pharmaceutical composition may also contain a peptide or a peptide fragment of at least one dimeric lytic protein derived from the same or different bacteria species, with an optional addition of one or more complementary agent, and a pharmaceutically acceptable carrier or diluent.

The present invention provides bacterial dimeric lysins, particularly recombinantly-generated dimeric lysins from naturally monomeric lysins, including comprising a dimeric Cpl-1 lysin polypeptide variant having bacterial killing activity. The invention describes dimeric Cpl-1 lysin mutants that contain mutant cysteines for dimerization and retain gram positive antibacterial activity. A composition is herein provided comprising a dimeric *Streptococcus* lysin, including a dimeric Cpl-1 mutant lysin, having equal or greater killing activity against *Streptococcus* cells, compared with the monomeric unmutated Cpl-1 lysin protein, including the dimeric CPl-1 lysin Cpl-1$^{C45S,D342C}$.

The present invention provides bacterial dimeric lysins, particularly recombinantly-generated dimeric lysins from naturally monomeric lysins, including comprising a dimeric Pal lysin polypeptide variant having bacterial killing activity. The invention describes dimeric Pal lysin mutants that contain mutant cysteines for dimerization and retain gram positive antibacterial activity. A composition is herein provided comprising a dimeric *Streptococcus* lysin, including a dimeric Pal mutant lysin, having equal or greater killing activity against *Streptococcus* cells, compared with the monomeric unmutated Pal lysin protein, including the dimeric Pal lysin p$_{a\ l}^{D280C}$.

The therapeutic composition may also comprise a holin protein. Holin proteins (or "holins") are proteins which produce holes in the cell membrane. Holin proteins may form lethal membrane lesions that terminate cellular respiration in a bacteria. Like the lytic proteins, holin proteins are coded for and carried by a phage. In fact, it is quite common for the genetic code of the holin protein to be next to or even within the code for the phage lytic protein. Most holin protein sequences are short, and overall, hydrophobic in nature, with a highly hydrophilic carboxy-terminal domain. In many cases, the putative holin protein is encoded on a different reading frame within the enzymatically active domain of the phage. In other cases, holin protein is encoded on the DNA next or close to the DNA coding for the cell wall lytic protein. Holin proteins are frequently synthesized during the late stage of phage infection and found in the cytoplasmic membrane where they cause membrane lesions. Holins can be grouped into two general classes based on primary structure analysis. Class I holins are usually 95 residues or longer and may have three potential transmembrane domains. Class II holins are usually smaller, at approximately 65-95 residues, with the distribution of charged and hydrophobic residues indicating two TM domains (Young, et al. Trends in Microbiology v. 8, No. 4, March 2000). At least for the phages of gram-positive hosts, however, the dual-component lysis system may not be universal. Although the presence of holins has been shown or suggested for several phages, no genes have yet been found encoding putative holins for all phages. Holins have been shown to be present in several bacteria, including, for example, lactococcal bacteriophage Tuc2009, lactococcal NLC3, pneumococcal bacteriophage EJ-1, *Lactobacillus gasseri* bacteriophage Nadh, *Staphylococcus aureus* bacteriophage Twort, *Listeria monocytogenes* bacteriophages, pneumococcal phage Cp-1, *Bacillus subtillis* phage M29, *Lactobacillus delbrueckki* bacteriophage LL-H lysin, and bacteriophage N 11 of *Staphyloccous aureus*. (Loessner, et al., Journal of Bacteriology, August 1999, p. 4452-4460).

For example, holin proteins can be used in conjunction with the lytic enzymes to accelerate the speed and efficiency at which the bacteria are killed. Holin proteins may also be in the form of chimeric and/or shuffled enzymes. Holin proteins may also be used alone in the treatment of bacterial infections according to some embodiments.

The pharmaceutical composition can contain a complementary agent, including one or more antimicrobial agent and/or one or more conventional antibiotics. In order to accelerate treatment of the infection, the therapeutic agent may further include at least one complementary agent which can also potentiate the bactericidal activity of the lytic enzyme. Antimicrobials act largely by interfering with the structure or function of a bacterial cell by inhibition of cell wall synthesis, inhibition of cell-membrane function and/or inhibition of metabolic functions, including protein and DNA synthesis. Antibiotics can be subgrouped broadly into those affecting cell wall peptidoglycan biosynthesis and those affecting DNA or protein synthesis in gram positive bacteria. Cell wall synthesis inhibitors, including penicillin and antibiotics like it, disrupt the rigid outer cell wall so that the relatively unsupported cell swells and eventually ruptures. Antibiotics affecting cell wall peptidoglycan biosynthesis include: Glycopeptides, which inhibit peptidoglycan synthesis by preventing the incorporation of N-acetylmuramic acid (NAM) and N-acetylglucosamine (NAG) peptide subunits into the peptidoglycan matrix. Available glycopeptides include vancomycin and teicoplanin; Penicillins, which act by inhibiting the formation of peptidoglycan cross-links. The functional group of penicillins, the β-lactam moiety, binds and inhibits DD-transpeptidase that links the peptidoglycan molecules in bacteria. Hydrolytic enzymes continue to break down the cell wall, causing cytolysis or death due to osmotic pressure. Common penicillins include oxacillin, ampicillin and cloxacillin; and Polypeptides, which interfere with the dephosphorylation of the Css-isoprenyl pyrophosphate, a molecule that carries peptidoglycan building-blocks outside of the plasma membrane. A cell wall-impacting polypeptide is bacitracin.

The complementary agent may be an antibiotic, such as erythromycin, clarithromycin, azithromycin, roxithromycin, vancomycin, oxacillin, doxycycline, other members of the macrolide family, penicilins, cephalosporins, and any combinations thereof in amounts which are effective to synergistically enhance the therapeutic effect of the lytic enzyme. The antibiotic or bacteriocidal or bacteriostatic agent(s) may be at concentrations or in amounts to clinically effect bacterial growth or viability or may be sub-MIC or below minimally inhibitory concentration does or amounts. Virtually any other antibiotic may be used with the altered and/or unaltered lytic enzyme. Similarly, other lytic enzymes may be included in the carrier to treat other bacterial infections.

Antibiotic supplements may be used in virtually all uses of the enzyme when treating different diseases. The pharmaceutical composition can also contain a peptide or a peptide fragment of at least one lytic protein, one holin protein, or at least one holin and one lytic protein, which lytic and holin proteins are each derived from the same or different bacteria species, with an optional addition of a complementary agents, and a suitable carrier or diluent.

Also provided are compositions containing nucleic acid molecules that, either alone or in combination with other nucleic acid molecules, are capable of expressing an effective amount of a dimeric lytic polypeptide(s) or a peptide fragment of a dimeric lytic polypeptide(s) in vivo. Cell cultures containing these nucleic acid molecules, polynucleotides, and vectors carrying and expressing these molecules in vitro or in vivo, are also provided.

Therapeutic or pharmaceutical compositions may comprise dimeric lytic polypeptide(s), including one or more dimeric lysin polypeptide(s) directed against the same, different, or overlapping susceptible bacteria, combined with a variety of carriers to treat the illnesses caused by the susceptible gram-positive bacteria. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, MgCl$_2$, CaCl$_2$, and others. Glycerin or glycerol (1,2,3-propanetriol) is commercially available for pharmaceutical use. It may be diluted in sterile water for injection, or sodium chloride injection, or other pharmaceutically acceptable aqueous injection fluid, and used in concentrations of 0.1 to 100% (v/v), preferably 1.0 to 50% more preferably about 20%. DMSO is an aprotic solvent with a remarkable ability to enhance penetration of many locally applied drugs. DMSO may be diluted in sterile water for injection, or sodium chloride injection, or other pharmaceutically acceptable aqueous injection fluid, and used in concentrations of 0.1 to 100% (v/v). The carrier vehicle may also include Ringer's solution, a buffered solution, and dextrose solution, particularly when an intravenous solution is prepared.

Any of the carriers for the dimeric lytic polypeptide(s) may be manufactured by conventional means. However, it is preferred that any mouthwash or similar type products not contain alcohol to prevent denaturing of the polypeptide/enzyme. Similarly, when the lytic polypeptide(s) is being placed in a cough drop, gum, candy or lozenge during the manufacturing process, such placement should be made prior to the hardening of the lozenge or candy but after the cough drop or candy has cooled somewhat, to avoid heat denaturation of the enzyme.

A dimeric lytic polypeptide(s) may be added to these substances in a liquid form or in a lyophilized state, where-upon it will be solubilized when it meets body fluids such as saliva. The polypeptide(s)/enzyme may also be in a micelle or liposome.

The effective dosage rates or amounts of a dimeric lytic enzyme/polypeptide(s) to treat the infection will depend in part on whether the dimeric lytic enzyme/polypeptide(s) will be used therapeutically or prophylactically, the duration of exposure of the recipient to the infectious bacteria, the size and weight of the individual, etc. The duration for use of the composition containing the enzyme/polypeptide(s) also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of enzyme believed to provide for an effective amount or dosage of enzyme may be in the range of about 100 units/ml to about 500,000 units/ml of fluid in the wet or damp environment of the nasal and oral passages, and possibly in the range of about 100 units/ml to about 50,000 units/ml. More specifically, time exposure to the active enzyme/polypeptide(s) units may influence the desired concentration of active enzyme units per ml. Carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depend on the nature of infection, whether treatment is to be prophylactic or therapeutic, and other variables. There are situations where it may be necessary to have a much higher unit/ml dosage or a lower unit/ml dosage.

The dimeric lytic enzyme/polypeptide(s) should be in an environment having a pH which allows for activity of the lytic enzyme/polypeptide(s). For example if a human individual has been exposed to another human with a bacterial upper respiratory disorder, the dimeric lytic enzyme/polypeptide(s) will reside in the mucosal lining and prevent any colonization of the infecting bacteria. Prior to, or at the time the dimeric lytic enzyme is put in the carrier system or oral delivery mode, it is preferred that the enzyme be in a stabilizing buffer environment for maintaining a pH range between about 4.0 and about 9.0, more preferably between about 5.5 and about 7.5.

A stabilizing buffer may allow for the optimum activity of the dimeric lysin enzyme/polypeptide(s). The buffer may contain a reducing reagent, such as dithiothreitol. The stabilizing buffer may also be or include a metal chelating reagent, such as ethylenediaminetetracetic acid disodium salt, or it may also contain a phosphate or citrate-phosphate buffer, or any other buffer. The DNA coding of these phages and other phages may be altered to allow a recombinant enzyme to attack one cell wall at more than two locations, to allow the recombinant enzyme to cleave the cell wall of more than one species of bacteria, to allow the recombinant enzyme to attack other bacteria, or any combinations thereof. The type and number of alterations to a recombinant bacteriophage produced enzyme are incalculable.

A mild surfactant can be included in a therapeutic or pharmaceutical composition in an amount effective to potentiate the therapeutic effect of the dimeric lytic enzyme/polypeptide(s) may be used in a composition. Suitable mild surfactants include, inter alia, esters of polyoxyethylene sorbitan and fatty acids (Tween series), octylphenoxy polyethoxy ethanol (Triton-X series), n-Octyl-.beta.-D-glucopyranoside, n-Octyl-.beta.-D-thioglucopyranoside, n-Decyl-.beta.-D-glucopyranoside, n-Dodecyl-.beta.-D-glucopyranoside, and biologically occurring surfactants, e.g., fatty acids, glycerides, monoglycerides, deoxycholate and esters of deoxycholate.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Pharmaceuticals or agents for use in all embodiments of the invention include antimicrobial agents, anti-inflammatory agents, antiviral agents, local anesthetic agents, corticosteroids, destructive therapy agents, antifungals, and antiandrogens. In the treatment of acne, active pharmaceuticals that may be used include antimicrobial agents, especially those having anti-inflammatory properties such as dapsone, erythromycin, minocycline, tetracycline, clindamycin, and other antimicrobials. The preferred weight percentages for the antimicrobials are 0.5% to 10%.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. A preferred concentration for local anesthetics is about 0.025% to 5% by weight of the total composition. Anesthetics such as benzocaine may also be used at a preferred concentration of about 2% to 25% by weight.

Corticosteroids that may be used include betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. Preferred concentrations for corticosteroids such as hydrocortisone or methylprednisolone acetate are from about 0.2% to about 5.0% by weight.

Additionally, the therapeutic composition may further comprise other enzymes, such as the enzyme lysostaphin for the treatment of any *Staphylococcus aureus* bacteria present along with the susceptible gram-positive bacteria. Mucolytic peptides, such as lysostaphin, have been suggested to be efficacious in the treatment of *S. aureus* infections of humans (Schaffner et al., Yale J. Biol. & Med., 39:230 (1967). Lysostaphin, a gene product of *Staphylococcus simulans*, exerts a bacteriostatic and bactericidal effect upon *S. aureus* by enzymatically degrading the polyglycine crosslinks of the cell wall (Browder et al., Res. Comm., 19: 393-400 (1965)). U.S. Pat. No. 3,278,378 describes fermentation methods for producing lysostaphin from culture media of *S. staphylolyticus*, later renamed *S. simulans*. Other methods for producing lysostaphin are further described in U.S. Pat. Nos. 3,398,056 and 3,594,284. The gene for lysostaphin has subsequently been cloned and sequenced (Recsei et al., Proc. Natl. Acad. Sci. USA, 84: 1127-1131 (1987)). The recombinant mucolytic bactericidal protein, such as r-lysostaphin, can potentially circumvent problems associated with current antibiotic therapy because of its targeted specificity, low toxicity and possible reduction of biologically active residues. Furthermore, lysostaphin is also active against non-dividing cells, while most antibiotics require actively dividing cells to mediate their effects (Dixon et al., Yale J. Biology and Medicine, 41: 62-68 (1968)). Lysostaphin, in combination with the altered lytic enzyme, can be used in the presence or absence of antibiotics. There is a degree of added importance in using both lysostaphin and the lysin enzyme in the same therapeutic agent. Frequently, when a human has a bacterial infection, the infection by one genus of bacteria weakens the human body or changes the bacterial flora of the body, allowing other potentially pathogenic bacteria to infect the body. One of the bacteria that sometimes co-infects a body is *Staphylococcus aureus*. Many strains of *Staphylococcus aureus* produce penicillinase, such that *Staphylococcus, Streptococcus*, and other Gram positive bacterial strains will not be killed by standard antibiotics. Consequently, the use of the lysin and lysostaphin, possibly in combination with antibiotics, can serve as the most rapid and effective treatment of bacterial infections. A therapeutic composition may also include mutanolysin, and lysozyme. A therapeutic or antibacterial composition may comprise combinations of dimeric lytic peptides, such as combinations of Cpl-1 dimer and Pal dimer.

Means of application of the therapeutic composition comprising a dimeric lytic enzyme/polypeptide(s) include, but are not limited to direct, indirect, carrier and special means or any combination of means. Direct application of the dimeric lytic enzyme/polypeptide(s) may be by any suitable means to directly bring the polypeptide in contact with the site of infection or bacterial colonization, such as to the nasal area (for example nasal sprays), dermal or skin applications (for example transdermal formulations, topical ointments or formulations), suppositories, tampon applications, etc. Nasal applications include for instance nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or the face or any combination of these and similar methods of application. The forms in which the dimeric lytic enzyme may be administered include but are not limited to lozenges, troches, candies, injectants, chewing gums, tablets, powders, sprays, liquids, ointments, and aerosols.

When the dimeric lytic enzyme(s)/polypeptide(s) is introduced directly by use of sprays, drops, ointments, washes, injections, packing and inhalers, the enzyme is preferably in a liquid or gel environment, with the liquid acting as the carrier. A dry anhydrous version of the altered enzyme may be administered by the inhaler and bronchial spray, although a liquid form of delivery is preferred.

A composition comprising a dimeric lytic enzyme/polypeptide(s) can be administered in the form of a candy, chewing gum, lozenge, troche, tablet, a powder, an aerosol, a liquid, a liquid spray, or toothpaste for the prevention or treatment of bacterial infections associated with upper respiratory tract illnesses. The lozenge, tablet, or gum into which the dimeric lytic enzyme/polypeptide(s) is added may contain sugar, corn syrup, a variety of dyes, non-sugar sweeteners, flavorings, any binders, or combinations thereof. Similarly, any gum-based products may contain acacia, carnauba wax, citric acid, cornstarch, food colorings, flavorings, non-sugar sweeteners, gelatin, glucose, glycerin, gum base, shellac, sodium saccharin, sugar, water, white wax, cellulose, other binders, and combinations thereof. Lozenges may further contain sucrose, cornstarch, acacia, gum tragacanth, anethole, linseed, oleoresin, mineral oil, and cellulose, other binders, and combinations thereof. Sugar substitutes can also be used in place of dextrose, sucrose, or other sugars.

Compositions comprising dimeric lytic enzymes, or their dimeric peptide fragments can be directed to the mucosal lining, where, in residence, they kill colonizing disease bacteria. The mucosal lining, as disclosed and described herein, includes, for example, the upper and lower respiratory tract, eye, buccal cavity, nose, rectum, vagina, periodontal pocket, intestines and colon. Due to natural eliminating or cleansing mechanisms of mucosal tissues, conventional dosage forms are not retained at the application site for any significant length of time.

It may be advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention. J. R. Robinson (U.S. Pat. No. 4,615,697, incorporated herein by reference) provides a good review of the various controlled release polymeric compositions used in mucosal drug delivery. The patent describes a controlled release treatment composition which includes a bioadhesive and an effective amount of a treating agent. The bioadhesive is a water swellable, but water insoluble fibrous, crosslinked, carboxy functional polymer containing (a) a plurality of repeating units of which at least about 80 percent contain at least one carboxyl functionality, and (b) about 0.05 to about 1.5 percent crosslinking agent substantially free from polyalkenyl polyether. While the polymers of Robinson are water swellable but insoluble, they are crosslinked, not thermoplastic, and are not as easy to formulate with active agents, and into the various dosage forms, as the copolymer systems of the present application. Micelles and multilamillar micelles may also be used to control the release of enzyme.

Other approaches involving mucoadhesives which are the combination of hydrophilic and hydrophobic materials, are known. Orahesive.®. from E.R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in this application produce an insoluble copolymer. U.S. Pat. No. 4,948,580, also incorporated by reference, describes a bioadhesive oral drug delivery system. The composition includes a freeze-dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 (incorporated herein by reference) discloses paste-like preparations comprising (A) a paste-like base comprising a polyorganosiloxane and a water soluble polymeric material which are preferably present in a ratio by weight from 3:6 to 6:3, and (B) an active ingredient. U.S. Pat. No. 5,554,380 claims a solid or semisolid bioadherent orally ingestible drug delivery system containing a water-in-oil system having at least two phases. One phase comprises from about 25% to about 75% by volume of an internal hydrophilic phase and the other phase comprises from about 23% to about 75% by volume of an external hydrophobic phase, wherein the external hydrophobic phase is comprised of three components: (a) an emulsifier, (b) a glyceride ester, and (c) a wax material. U.S. Pat. No.

5,942,243 describes some representative release materials useful for administering antibacterial agents, which are incorporated by reference.

Therapeutic or pharmaceutical compositions can also contain polymeric mucoadhesives including a graft copolymer comprising a hydrophilic main chain and hydrophobic graft chains for controlled release of biologically active agents. The graft copolymer is a reaction product of (1) a polystyrene macromonomer having an ethylenically unsaturated functional group, and (2) at least one hydrophilic acidic monomer having an ethylenically unsaturated functional group. The graft chains consist essentially of polystyrene, and the main polymer chain of hydrophilic monomeric moieties, some of which have acidic functionality. The weight percent of the polystyrene macromonomer in the graft copolymer is between about 1 and about 20% and the weight percent of the total hydrophilic monomer in the graft copolymer is between 80 and 99%, and wherein at least 10% of said total hydrophilic monomer is acidic, said graft copolymer when fully hydrated having an equilibrium water content of at least 90%. Compositions containing the copolymers gradually hydrate by sorption of tissue fluids at the application site to yield a very soft jelly like mass exhibiting adhesion to the mucosal surface. During the period of time the composition is adhering to the mucosal surface, it provides sustained release of the pharmacologically active agent, which is absorbed by the mucosal tissue.

The compositions of this application may optionally contain other polymeric materials, such as poly(acrylic acid), poly,-(vinyl pyrrolidone), and sodium carboxymethyl cellulose plasticizers, and other pharmaceutically acceptable excipients in amounts that do not cause deleterious effect upon mucoadhesivity of the composition.

The dosage forms of the compositions of this invention can be prepared by conventional methods. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. A vasoconstriction agent can be added to the formulation. The pharmaceutical preparations according to this application are provided sterile and pyrogen free.

A dimeric lytic enzyme/polypeptide(s) of the invention may also be administered parenterally. For example, the dimeric lytic enzyme/polypeptide(s) can be administered intramuscularly, intrathecally, subdermally, subcutaneously, or intravenously to treat infections by gram-positive bacteria. In cases where parenteral injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin A vasoconstriction agent can be added to the formulation. The pharmaceutical preparations according to this application are provided sterile and pyrogen free.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The effective dosage rates or amounts of the dimeric lytic enzyme/polypeptide(s) to be administered parenterally, and the duration of treatment will depend in part on the seriousness of the infection, the weight of the patient, particularly human, the duration of exposure of the recipient to the infectious bacteria, the number of square centimeters of skin or tissue which are infected, the depth of the infection, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzymes believed to provide for an effective amount or dosage of enzymes may be selected as appropriate. The amount of active units per ml and the duration of time of exposure depend on the nature of infection, and the amount of contact the carrier allows the lytic enzyme(s)/polypeptide(s) to have.

Methods and Assays

The bacterial killing capability, and indeed the significantly improved stability and decreased plasma clearance, exhibited by the lysin polypeptide(s) of the invention provides for various methods based on the antibacterial effectiveness of the polypeptide(s) of the invention. Thus, the present invention contemplates antibacterial methods, including methods for killing of gram-positive bacteria, for reducing a population of gram-positive bacteria, for treating or alleviating a bacterial infection, for treating a human subject exposed to a pathogenic bacteria, and for treating a human subject at risk for such exposure. The susceptible bacteria may be readily determined or confirmed by the skilled artisan and also are demonstrated herein to include the bacteria from which the phage enzyme(s) of the invention are originally derived, Streptococcus pneumoniae, as well as various other Streptococcal bacterial strains. Methods of treating various conditions are also provided, including methods of prophylactic treatment of Streptococcal infections, treatment of Streptococcal infections, reducing Streptococcal polulation or carriage, treating lower respiratory infection, treating ear infection, treating ottis media, treating endocarditis, and treating or preventing other local or systemic infections or conditions.

This invention may also be used to treat septicemia, particularly in a human. For the treatment of a septicemic infection, such as for *pneumoniae*, or bacterial meningitis, there should be a continuous intravenous flow of therapeutic agent into the blood stream. The concentration of the enzymes for the treatment of septicemia is dependent upon the bacterial count in the blood and the blood volume.

Also provided is a method for treating Streptococcal infection, carriage or populations comprises treating the infection with a therapeutic agent comprising an effective amount of at least one dimeric lytic enzyme(s)/polypeptide(s) of the invention, particularly dimeric Cpl-1 lysin, including as particularly described herein. More specifically, dimeric lytic enzyme/polypeptide capable of lysing the cell wall of Streptococcal bacterial strains is produced from genetic material from a bacteriophage specific for *Streptococcus* or from one or more plasimid, vector, or other recombinant means. In the methods of the invention, the dimeric lysin polypeptide(s) of the present invention, including Cpl-1 dineric lysin, are useful and capable in prophylactic and treatment methods directed against gram-positive bacteria, particularly Streptococcal infections or bacterial colonization. Bacterial strains susceptible and relevant as targets in the methods of the invention include and may be selected from *Streptococcus suis, Streptococcus equi, Streptococcus agalactiae* (GBS), *Streptococcus pyogenes* (GAS), *Streptococcus sanguinis, Streptococcus gordonii, Streptococcus dysgalactiae, Streptococcus* GES and *Streptococcus pneumonia*.

The invention includes methods of decolonizing, treating or alleviating Streptoccal related infections or conditions, including antibiotic-resistant bacteria, wherein the bacteria or a human subject infected by or exposed to the particular bacteria, or suspected of being exposed or at risk, is contacted with or administered an amount of isolated dimeric lysin polypeptide(s) of the invention effective to kill the particular bacteria. Thus, one or more of dimeric Cpl-1, including such polypeptides as provided herein and in FIG. 6 and Table 1 and SEQ ID NO: 3, is contacted or administered so as to be effective to kill the relevant bacteria, decolonize the relevant bacteria, or otherwise alleviate or treat the bacterial infection. In a further or additional aspect, one or more of dimeric Pal, including such polypeptides as provided herein and in FIG. 7 and SEQ ID NOL 6, is contacted or administered so as to be effective to kill the relevant bacteria or otherwise alleviate or treat the bacterial infection.

The term 'agent' means any molecule, including polypeptides, antibodies, polynucleotides, chemical compounds and small molecules. In particular the term agent includes compounds such as test compounds, added additional compound(s), or lysin enzyme compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, polypeptide, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of infection of gram-positive bacteria, including having a bacteriocidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

It is noted that in the context of treatment methods which are carried out in vivo or medical and clinical treatment methods in accordance with the present application and claims, the term subject, patient or individual is intended to refer to a human.

The terms "gram-positive bacteria", "Gram-positive bacteria", "gram-positive" and any variants not specifically listed, may be used herein interchangeably, and as used throughout the present application and claims refer to Gram-positive bacteria which are known and/or can be identified by the presence of certain cell wall and/or cell membrane characteristics and/or by staining with Gram stain. Gram positive bacteria are known and can readily be identified and may be selected from but are not limited to the genera *Listeria, Staphylococcus, Streptococcus, Enterococcus, Mycobacterium, Corynebacterium,* and *Clostridium,* and include any and all recognized or unrecognized species or strains thereof.

The term "bacteriocidal" refers to capable of killing bacterial cells.

The term "bacteriostatic" refers to capable of inhibiting bacterial growth, including inhibiting growing bacterial cells.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

Diseases or conditions caused by a streptococcal infection (such as those caused by *Streptococcus pneumoniae*, may be treated by administering a composition comprising a therapeutically effective amount of a dimeric lysin to a mammal suffering from a disease or condition. In certain embodiments, the disease or condition is bacteremia, meningitis, pneumonia, otitis media, or sinusitis.

One method for treating systemic or tissue bacterial infections caused by *Streptococcus* bacteria comprises parenterally treating the infection with a therapeutic agent comprising an effective amount of one or more dimeric lysin polypeptide(s) of the invention, particularly dimeric Cpl-1 including such polypeptides as provided herein in FIG. 6 and Table 1, and/or dimeric Pal including polypeptides as provided herein in FIG. 7 and SEQ ID NO: 6, and an appropriate carrier. A number of other different methods may be used to introduce the dimeric lytic enzyme(s)/polypeptide(s). These methods include introducing the dimeric lytic enzyme(s)/polypeptide(s) intravenously, intramuscularly, subcutaneously, intrathecally, and subdermally. One skilled in the art, including medical personnel, will be capable of evaluating and recognizing the most appropriate mode or means of administration, given the nature and extent of the bacterial condition and the strain or type of bacteria involved or suspected. For instance, intrathecal use and administration of one or more dimeric lytic polypeptide(s) would be most beneficial for treatment of bacterial meningitis.

Infections may be also be treated by injecting into the infected tissue of the human patient a therapeutic agent comprising the appropriate lytic enzyme(s)/polypeptide(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene-diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils, liposomes, and ethyl oleate are also useful herein. Other phage associated lytic enzymes, along with a holin protein, may be included in the composition.

Various methods of treatment are provided for using a dimeric lytic enzyme/polypeptide(s), such as dimeric Cpl-1 lysin or dimeric Pal lysin, or combinations thereof or therewith, as exemplified herein, as a prophylactic treatment for eliminating or reducing the carriage of susceptible bacteria, preventing those humans who have been exposed to others who have the symptoms of an infection from getting sick, or as a therapeutic treatment for those who have already become ill from the infection. Similarly, the dimeric lytic enzyme(s)/polypeptide(s) can be used to treat or alleviate, for example, lower respiratory tract illnesses, particularly by the use of bronchial sprays or intravenous administration of the enzyme. For example, a lytic enzyme can be used for the prophylactic and therapeutic treatment of eye infections, such as conjunctivitis. The method of treatment comprises administering eye drops or an eye wash which comprise an effective amount of at least one dimeric lytic polypeptide(s) of the invention and a carrier capable of being safely applied to an eye, with the carrier containing the lytic enzymes. The eye drops or eye wash are preferably in the form of an isotonic solution. The pH of the solution should be adjusted so that there is no irritation of the eye, which in turn would lead to possible infection by other organisms, and possible damage to the eye. While the pH range should be in the same range as for other lytic enzymes, the most optimal pH will be in the range as demonstrated and provided herein. Similarly, buffers of the sort described above for the other lytic enzymes should also be used. Other antibiotics which are suitable for use in eye drops may be added to the composition containing the enzymes. Bactericides and bacteriostatic compounds may also be added. The concentration of the enzyme(s) in the solution can be in the range of from about 100 units/ml to about 500,000 units/ml, with a more preferred range of about 100 to about 5,000 units/mil, and about 100 to about 50,000 units/ml. Concentrations can be higher or lower than the ranges provided.

The dimeric lytic polypeptide(s) of the invention may also be used in a contact lens solution, for the soaking and cleaning of contact lenses. This solution, which is normally an isotonic solution, may contain, in addition to the enzyme, sodium chloride, mannitol and other sugar alcohols, borates, preservatives, and the like. A lytic enzyme/polypeptide of the invention may also be administered to the ear of a patient. Thus, for instance a dimeric lytic polypeptide(s) of the invention may be used to treat ear infections, for example caused by *Streptococcus pneumoniae*. Otitis media is an inflammation of the middle ear characterized by symptoms such as otalgia, hearing loss and fever. One of the primary causes of these symptoms is a build up of fluid (effusion) in the middle ear. Complications include permanent hearing loss, perforation of the tympanic membrane, acquired cholesteatoma, mastoiditis, and adhesive otitis. Children who develop otitis media in the first years of life are at risk for recurrent acute or chronic disease. One of the primary causes of otitis media is *Streptococcus pneumoniae*. The lytic enzyme(s)/polypeptide(s) may be applied to an infected ear by delivering the enzyme(s) in an appropriate carrier to the canal of the ear. The carrier may comprise sterile aqueous or oily solutions or suspensions. The lytic enzyme(s) may be added to the carrier, which may also contain suitable preservatives, and preferably a surface-active agent. Bactericidal and fungicidal agents preferably included in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol. Additionally, any number of other eardrop carriers may be used. The concentrations and preservatives used for the treatment of otitis media and other similar ear infections are the same as discussed for eye infections, and the carrier into which the enzyme goes is similar or identical to the carriers for treatment of eye infections. Additionally, the carrier may typically includes vitamins, minerals, carbohydrates, sugars, amino acids, proteinaceous materials, fatty acids, phospholipids, antioxidants, phenolic compounds, isotonic solutions, oil based solutions, oil based suspensions, and combinations thereof.

The diagnostic, prophylactic and therapeutic possibilities and applications that are raised by the recognition of and generation of the dimeric lysin polypeptide(s) of the invention, derive from the fact that the polypeptides of the invention cause direct and specific effects (e.g. killing) in susceptible bacteria. Thus the polypeptides of the invention may be used to eliminate, characterize, or identify the relevant and susceptible bacteria.

Thus, a diagnostic method of the present invention may comprise examining a cellular sample or medium for the purpose of determining whether it contains susceptible bacteria, or whether the bacteria in the sample or medium are susceptible by means of an assay including an effective amount of one or more dimeric lysin polypeptide(s) and a means for characterizing one or more cell in the sample, or for determining whether or not cell lysis has occurred or is occurring. Patients capable of benefiting from this method include those suffering from an undetermined infection, a recognized bacterial infection, or suspected of being exposed to or carrying a particular bacteria. A fluid, food, medical device, composition or other such sample which will come in contact with a subject or patient may be examined for susceptible bacteria or may be eliminated of relevant bacteria. In one such aspect a fluid, food, medical device, composition or other such sample may be sterilized or otherwise treated to eliminate or remove any potential relevant bacteria by incubation with or exposure to one or more lytic polypeptide(s) of the invention.

The procedures and their application are all familiar to those skilled in the art and accordingly may be utilized within the scope of the present invention. In one instance, the lytic polypeptide(s) of the invention complex(es) with or otherwise binds or associates with relevant or susceptible bacteria in a sample and one member of the complex is labeled with a detectable label. The fact that a complex has formed and, if desired, the amount thereof, can be determined by known methods applicable to the detection of labels. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, B-glucuronidase, B-D-glucosidase, B-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

A Stable Phage Lysin (Cpl-1) Dimer with Increased Anti-Pneumococcal Activity

Bacteriophages (phages) produce endolysins (lysins) as part of their lytic cycle to degrade the peptidoglycan layer of the infected bacteria for the release of phage progeny. Because these enzymes keep their lytic and lethal activity against gram-positive bacteria when added extrinsically to the cells, they have been actively exploited as novel anti-infectives sometimes termed enzybiotics. As other relatively small peptides, one issue in their clinical development is rapid inactivation through proteolytic degradation, immunologic blockage, or renal clearance. The anti-pneumococcal lysin Cpl-1 was shown to escape both proteolysis and immunological blockage. However, its short plasma half-life (20.5 min. in mice) may represent a shortcoming for clinical usefulness. Here we report the construction of a Cpl-1 dimer, in view of increasing both Cpl-1 anti-pneumococcal specific activity and plasma half-life. Dimerization was achieved by introducing specific cysteine residues at the C-terminal of the enzyme, thus favoring disulfide bonding. Compared to the native monomers, the constructed dimer demonstrated a 2-fold increase in specific anti-pneumococcal activity, and a nearly 10-fold increase in plasma half-life (i.e. 0.028 vs 0.27 ml.min$^{-1}$). As several lysins are suspected to dimerize on contact with their cell wall substrate to be fully active, stable pre-dimerized enzymes may represent a more efficient alternative to the native monomer.

*Streptococcus pneumoniae* (*S. pneumoniae*) is an encapsulated gram-positive diplococcus responsible for a wide variety of human infections. It is the first cause of otitis media, affecting >5 million children each year in the USA (4), and a common cause of sinusitis, community-acquired pneumonia, bacteremia and meningitis (13). It is responsible for >1 million deaths/year among children below 5 years old worldwide (5), and pneumococcal pneumonia remains the sixth most common cause of death in the USA for all age groups (8). *S. pneumoniae* is also the primary bacterial pathogen responsible for super-infection following Influenza A respiratory infection, a complication accounting for >90% of deaths during influenza pandemics (2, 3, 20, 21).

Pneumococcal infections are usually treated with antibiotics. However, their overuse in the treatment of millions of mild cases of otitis and sinusitis, mostly of viral origin, has put an enormous pressure for the selection of resistances (11). Hence, bacteriologically confirmed treatment failures are now widely reported, due to an increase in resistance to numerous drug classes, including commonly used beta-lactams, macrolides and fluoroquinolones (19, 23). Thus, new drugs acting by totally different mechanisms are highly desired.

Phages, which are major predators of bacteria in nature, were viewed as potential anti-bacterial agents decades before the clinical development of antibiotics (28, 29). Nevertheless, the complexity of developing native phages to amenable industrial products led Western countries to abandon its development since the 1940's. Today, however, the problematic expansion of antibiotic resistances justifies the renewed interest in the contribution of phage-derived molecules as potential clinically useful anti-bacterial compounds (9, 27).

One of these compound classes, i.e. phage lysins, has been exploited for its rapid killing action on gram-positive bacteria (1, 9). Phage lysins are timely produced when the phage progeny needs to escape the bacterial host. Pneumococcal phage Cp-1 produces the lysin Cpl-1, a 37 kDa enzyme that specifically hydrolyses pneumococcal peptidoglycan. This lysin is constructed like all such endolysins, having two well-defined domains connected by a flexible linker. The catalytic activity is restricted to the N-terminal domain, while the C-terminal part, containing 6 choline-binding repeats (ChBR) and a C-terminal tail of 13 amino-acids, is required for specific substrate binding in the pneumococcal cell wall (10). Cpl-1 belongs to the family of lysozymes which target the β1,4 linkages between N-acetyl-muramic acid and N-acetyl-D-glucosamine residues in the peptidoglycan (22). Our laboratory cloned the Cpl-1 gene into the high expression vector pinlllA and achieved its over-expression and purification (15). Purified Cpl-1 successfully treated pneumococcal sepsis (14, 16), endocarditis (6), meningitis (12), and pneumonia (31) in rodent models. Nevertheless, Cpl-1 was quickly cleared from the blood in vivo, and repeated injections or continuous infusion was required to optimize activity in some infection models (6, 31). This short half-life may be a shortcoming for the clinical development of Cpl-1 and similar lysins.

To construct a more effective Cpl-1 we took advantage of recent knowledge on lysin dimerization. To be fully active, the major pneumococcal autolysin (LytA) requires prior dimerization, which is initiated by the interaction of its C-terminal choline-binding domains with choline, leading to the formation of a homodimer that is significantly more active than the native monomer (7, 26, 30). Sequence alignment of Cpl-1 and LytA revealed extensive similarities, especially within the C-terminal tail of the enzyme involved in dimerization. Thus, we hypothesized that Cpl-1 may have the same dimerizing requirement as that of LytA for full activity. In addition, the dimeric form of Cpl-1 could have a significant decrease in renal clearance because its molecular weight (74 kDa versus 37 kDa for the monomer) is greater than 60-65 kDa, the threshold for glomerular filtration in humans (18).

In this work we constructed a stable Cpl-1 homodimer linked at the C-terminus by a disulfide bond, and examined its in vitro activity and in vivo plasma clearance compared to the parental monomer. The results provide the basis for further studying the bioactivity of this type of dimer in infection models.

Materials and Methods

Reagents

Plasmid minipreps kit was from Qiagen (Valencia, USA) and QuickChange II Site-Directed Mutagenesis Kit was from Stratagene (Cedar Creek, USA). DEAE-Sepharose and the gel filtration HiLoad 16/60 Superdex™ 200 prep grade column were obtained from GE Healthcare Bio-Sciences Corporation (Piscataway, USA). Mutagenic primers were synthesized by Fisher Scientific (Pittsburgh, USA). All other chemicals were purchased from Sigma-Aldrich (Saint Louis, USA). The Quick Start Bradford dye reagent and the bovine gamma globulin (BGG) standards for protein concentrations measurements were from Biorad (Hercules, USA). Amicon ultra centrifugal devices were purchased from Millipore (Billerica, USA) and 0.45 µm Acrodisc syringe filters from Pall (Ann Arbor, USA).

Construction of Cpl-1 Mutants

All mutants were constructed using the QuickChange II Site-Directed Mutagenesis Kit with appropriate primers to introduce the desired mutations, and following the manufacturer instructions. The presence of the mutations was verified by DNA sequencing performed at Genewiz (South Plainfield, N.J. USA).

Production and Purification of the Cpl-1 and Cpl-1 Mutant Lysins

Plasmid DNAs from selected clones carrying the wild-type and mutated Cpl-1 genes were isolated and further transformed into E. coli DH5α in order to over-express the corresponding proteins. The wild-type Cpl-1 protein was obtained from the expression of pJML6 in DH5α E. coli cells. The production and purification of the lysins followed the procedure already described elsewhere (15). Briefly, the strains were grown overnight at 37° C. in Luria-Broth under agitation at 225 rpm. Protein expression was induced overnight with 20 g/L of lactose. After harvesting and resuspension in enzyme buffer (50 mM phosphate buffer, pH 7.4), the cells were sonicated on ice (Sonopuls, Bandelin electronics, Berlin, Germany). The cell debris was pelleted by centrifugation (15,000 rpm, 1 h at 37° C.) and the supernatants treated with 20 units (20 U) of DNAse I for 1 h at room temperature. The 0.45 µm filtered supernatants were applied to a DEAE-Sepharose fast flow column previously equilibrated with enzyme buffer. Following a washing step with enzyme buffer containing 1M NaCl, the enzymes were eluted with enzyme buffer containing 10% choline. After extensive dialysis (MWCO 12-14,000) against enzyme buffer, the purified enzymes were lyophilized and stored at −20° C.

Isolation of the Cpl-1 Mutant Dimers

All dimers were further isolated on a Hiload 16/60 Superdex column connected to the AKTA Prime apparatus (GE Healthcare Bio-Sciences Corporation, Piscataway, USA). Briefly, for each mutant, the mixture of monomers and dimers spontaneously obtained after over-expression by lactose induction (see above), was applied at 1 ml/min. to the column previously equilibrated with enzyme buffer. Fractions containing the dimers were pooled, and concentrated with Amicon Ultra centrifugal filter units (MWCO 30,000, Millipore, Carrigtwohill, Ireland) following manufacturer recommendations. A second purification step on Hiload 16/60 Superdex was performed with the concentrated sample. The final fractions containing the dimers were pooled, concentrated to 1 mg/ml, and stored at −20° C. until further use.

In Vitro Killing Assay

The killing assay was performed using the S. pneumoniae strain DCC1490 and has been described elsewhere (17). Briefly, DCC1490 was grown to log-phase ($OD_{595nm}$ of 0.3) in Brain Heart Infusion (BHI). After centrifugation and resuspension of the cells in enzyme buffer to a concentration of approximately $10^9$ CFU/ml, serial dilutions of the lysins were directly added to the bacterial suspension (final concentration of approximately $5.10^8$ CFU/ml) in 96-well plates. The reaction kinetics was obtained by measuring the $OD_{595nm}$ at 37° C. over a period of 15 minutes in an EL808 96-well plate reader (Biotek Instruments, Luzern, Switzerland). 1 U of enzyme was defined as the amount of enzyme required to achieve a decrease by half of the $OD_{595nm}$ (corresponding to 1 log decrease in CFU/ml) of a $5.10^8$ CFU/ml solution of S. pneumoniae DCC1490 after 15 minutes at 37° C.

Measurement of Lysin Clearance in Mouse Plasma

All animal experiments were carried out according to Federal and Institutional guidelines. Male Balb/c mice with an average weight of 22 g, obtained from Charles River Laboratories (Wilmington, USA), were intravenously (iv) injected in the lateral tail vein with the same amount of mol of both the wild-type and dimeric Cpl-1 enzymes. Thus, single bolus (100 µl) of either Cpl-1 (4.5 mg/ml) or Cpl-$1^{C45S,D324C}$ dimer (9 mg/ml) were administered to two distinct groups of 15 mice. After anesthesia, blood samples were collected by cardiac puncture 5, 30, 60, 180 and 300 mM. post-administration and directly placed on ice.

Plasma was prepared from ice-cold heparinized blood samples by centrifugation at 3000×g for 10 min. at 4° C. Plasma samples were stored at −20° C. until use. Plasma concentrations of Cpl-1 and Cpl-$1^{C45S,D324C}$ dimer were determined using an indirect sandwich ELISA assay. 96 well plates were coated with a 5 µg/ml solution of monoclonal anti-Cpl1 antibody in phosphate buffer saline IX (PBS IX), pH 7.4 (3 h at 37° C. and then overnight at 4° C.). After 5 washes with 200 μï of wash buffer (PBS IX, NaCl 150 mM, Brij-35 0.05%, sodium azide 0.02%, pH 7.4), 100 μï of the plasma samples and standards diluted in dilution buffer (PBS IX, 0.5 M NaCl, 0.25% Brij-35, 0.02% sodium azide, pH 7.4) were added to the wells and plates incubated for 3 h at 37° C. Plates were further washed 5 times with 200 μï wash buffer, and 100 μï/well of primary antibody (rabbit polyclonal anti-Cpl-1 antibody) diluted to 2 μï/ml in dilution buffer were added to the wells, and plates incubated for another 3 h at 37° C. Following 5 additional washes with 200 μï wash buffer, the plates were incubated overnight at room temperature in the presence of 100 μï/well of the secondary antibody (alkaline phosphatase conjugated goat anti-rabbit-IgG) diluted to 1/1000 in dilution buffer. The following morning, wells were washed 5 times with 200 μï wash buffer, and enzymatic activity was measured at 405 nm by colorimetric detection after incubation with 200 μï of the alkaline phosphatase substrate (1 mg/ml in 10% diethanolamine, 1 mM $MgCl_2$) at room temperature. A Spectra Max $5^e$ plate reader (Molecular Devices, Sunnyvale, USA) was used, and results were analyzed with the SoftMax Pro software.

Since the monomeric and the dimeric forms of Cpl-1 react differently with the Cpl-1-specific antibodies, it was necessary to use two different standards in the ELISA assay. Purified Cpl-1 monomers of known concentrations were used in the experiments with the native enzyme and purified Cpl-1$^{C45S,D324C}$ dimers of known concentrations were used for the experiments with Cpl-1$^{C45S,D324C}$ dimer.

Results and Discussion

It was recognized that the amino acid sequences of the C-terminal regions of LytA and Cpl-1 were homologous (73/142 identical residues, and 55/69 residues are conservative substitutions), and that the C-terminal 13 amino acids were responsible for the dimerization of LytA (FIG. 1). Interestingly, within this region 10/13 amino acids are identical between Cpl-1 and LytA. We thus speculated that Cpl-1 might also dimerize to become fully active.

Construction and Purification of Cpl-1$^{C45S,D324C}$ Dimer

Our strategy to create a pre-dimerized enzyme was centered on the formation of a disulfide bridge between two monomers. The wild-type Cpl-1 enzyme contains three cysteine residues at position 45, 108, and 239. Using the Accpro server under the SCRATCH protein predicator website (scratch.proteomics.ics.uci.edu/index), only cysteine 45 (C45) was predicted to be accessible to the solvent. Thus, to avoid possible interactions with this cysteine residue we engineered the mutant Cpl-1$^{C45S}$. This mutant was soluble and fully active compared to native Cpl-1 (data not shown).

Figure 2B:
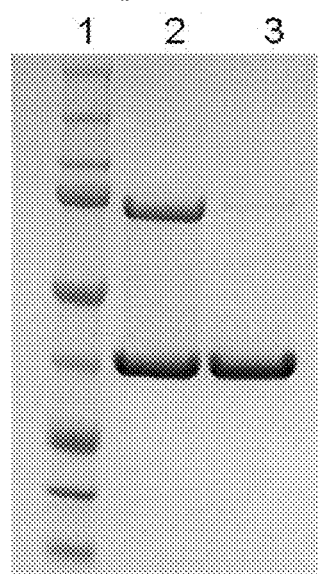
Figure 2C:
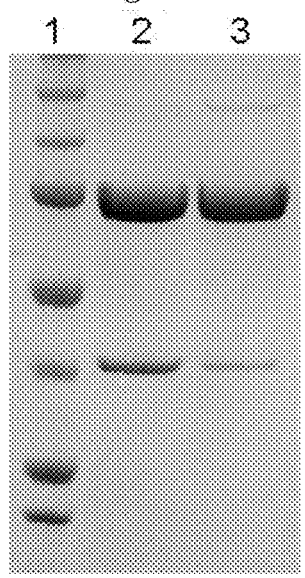

To construct the pre-dimerized form of Cpl-1, we further mutated Cpl-1$^{C45S}$ to Cpl-1$^{C45S,D324C}$. We specifically introduced the new cysteine residue prior to the 13 amino-acid stretch in the C-terminal tail of Cpl-1 to prevent disturbance of the critical structure in this region. The mutation was confirmed by DNA sequencing. Cpl-1 and Cpl-1$^{C45S,D324C}$ were successfully over-expressed in E. coli DH5a cells and purified to homogeneity on a DEAE-Sepharose column (FIG. 2A, lane 2, and FIG. 2B, lane 2). As predicted for Cpl-1$^{C45S,D324C}$, a second band spontaneously appeared at 74 kDa on the Coomassie stained non-reducing SDS-PAGE gel (FIG. 2B, lane 2). Reduction of this sample with 10 mM dithiothreitol (DTT), led to the total disappearance of the 74 kDa band (FIG. 2B, lane 3), confirming that the disulfide bond-related dimeric form of Cpl-1$^{C45S,D324C}$ was reducible. Further purification to homogeneity (~94%) of the Cpl-1$^{C45S,D324C}$ dimer was achieved by a two step purification process on Sephadex G-100, (FIG. 2C, lanes 2, and 3).

In Vitro Anti-microbial Activity of Cpl-1$^{C45S,D324C}$ Monomers

Figure 3:
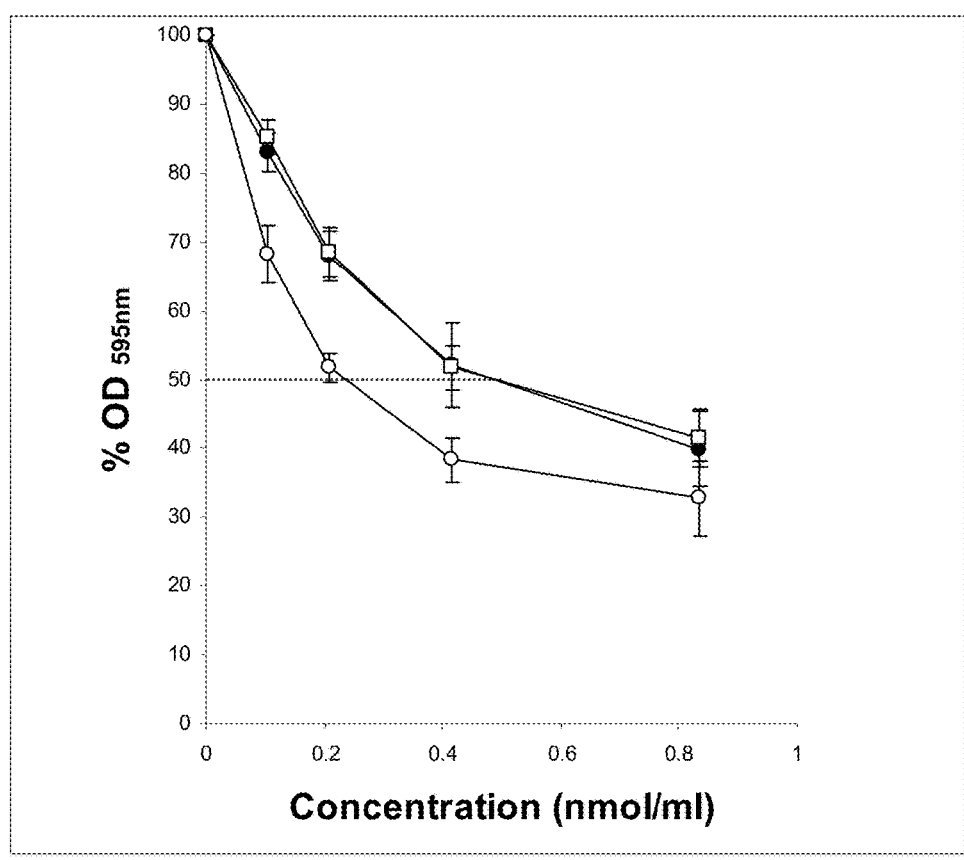
FIG. 3 shows in vitro anti-bacterial activity of Cpl-1 on a $5.10^8$ CFU/ml suspension of *S. pneumoniae* DCC1490 after 15 minutes incubation at 37° C. Cpl-1 wt (filled circles), Cpl-$1^{C45S,D324C}$ monomeric form in 1 mM DTT (open squares), and Cpl-$1^{C45S,D324C}$ dimer (open circles). n=4 for each enzyme and condition.

We found that 1 mM DTT was sufficient to achieve complete reduction of the Cpl-1$^{C45S,D324C}$ dimer into monomers (data not shown). In this experiment, the anti-microbial activity of purified Cpl-1$^{C45S,D324C}$ monomeric form was therefore measured in the presence of 1 mM DTT. Under this condition, the mutant enzyme retained 100% of the in vitro anti-bacterial activity compared to native Cpl-1. As seen in FIG. 3, using the in vitro killing assay, a 50% decrease of the OD595 nm of S. pneumoniae was achieved after 15 minutes at 0.5 nmol/ml with both Cpl-1 and Cpl-1$^{C45S,D324C}$ monomers. The calculated specific activities were 6.7 U/nmol of enzyme in both cases. It can be concluded that the replacement of an aspartic acid with a cysteine within the C-terminal region has no significant effect on the activity of Cpl-1$^{C45S,D324C}$. The substitution being located just before the 13 amino acids tail needed for native dimerization of LytA (and possibly Cpl-1), it can therefore be concluded that the new cysteine residue does not interfere with the suspected Cpl-1 natural dimerization process required for full activity. Finally, we speculate that Cpl-1$^{C45S,D324C}$, when converted into monomers by DTT treatment, re-associates with the same efficacy into dimers when it interacts with the choline in the cell wall.

In Vitro Anti-microbial Activity of Cpl-1$^{C45S,D324C}$ Dimers

In our in vitro assay purified Cpl-1$^{C45S,D324C}$ dimers (FIG. 2C, lane 3) showed an increased anti-bacterial activity by a factor of 2 when compared to Cpl-1 (50% ODsgsnm decrease achieved by 0.25 versus 0.5 nmol/ml, for Cpl-1$^{C45S,D324C}$ dimer and Cpl-1 respectively (FIG. 3). The calculated specific activities were 13.33 and 6.67 U/nmol, for Cpl-1$^{C45S,D324C}$ dimers and Cpl-1, respectively. This observation is not surprising since on a mole-to-mole basis, twice as many molecules of monomers are required to produce a fixed number of dimers. Moreover, the dimers contain two active site (versus one in the monomer) and were therefore expected to have twice the activity of the monomers. Finally, this result provided us with the evidence that C-terminal dimerization does not impair Cpl-1 activity, i.e. if a LytA-like dimerization occurs in nature for Cpl-1, it would not impair the enzyme activity.

Only CPl-1$^{C45S,D324C}$ Dimer is Fully Active

Figure 5:
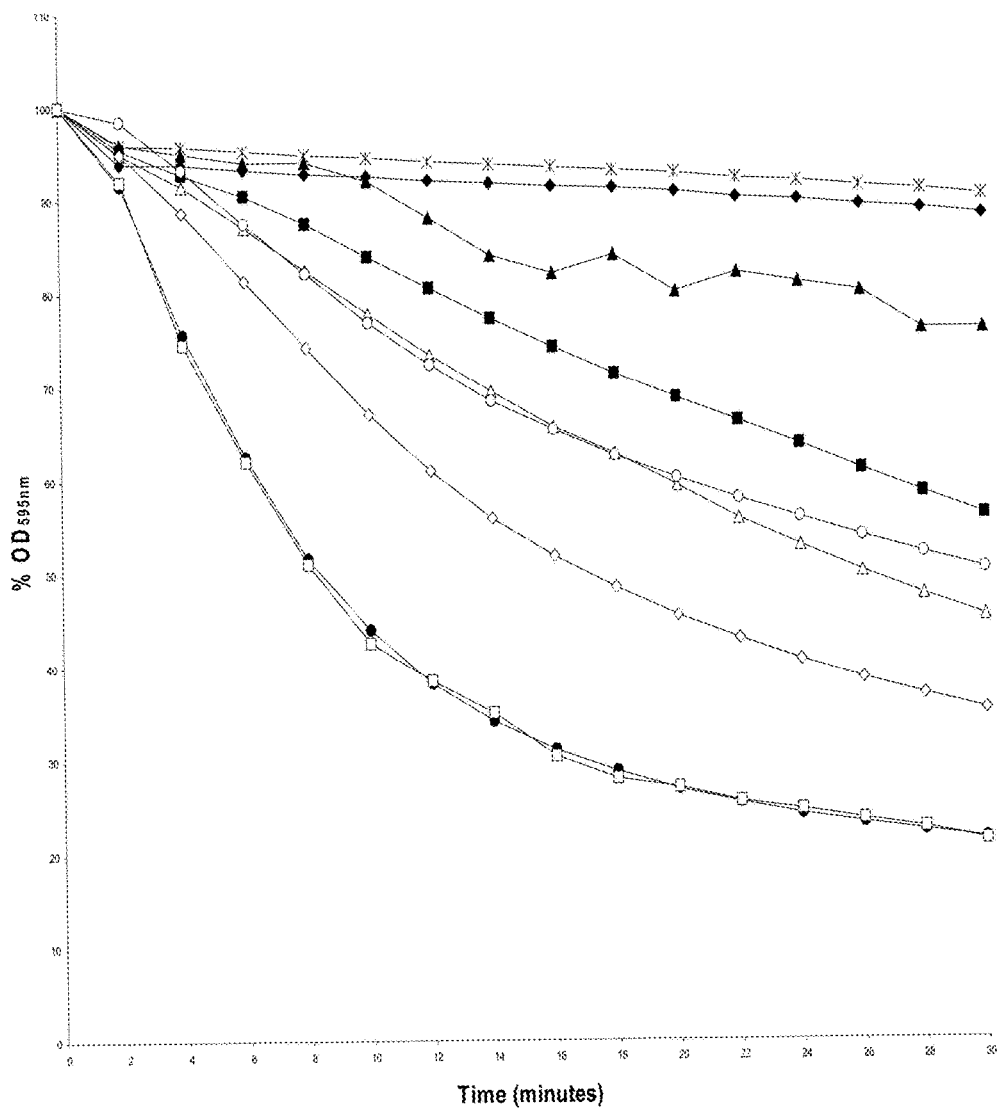
FIG. 5. In vitro anti-microbial activity of several purified Cpl-1 mutant dimers on a $5.10^8$ CFU/ml suspension of *S. pneumoniae* DCC1490 at 37° C. Cpl-1 wt (filled circles), Cpl-$1^{C45S,Q85C}$ dimer (filled diamonds)5 Cpl-$1^{C45S,D194C}$ dimer (filled triangles)5 Cpl-$1^{C45S,N214C}$ dimer (filled squares), Cpl-$1^{C45S,G216C}$ dimer (open triangles), Cpl-$1^{C45S,D256C}$ dimer (open diamonds), Cpl-$1^{C45S,S269C}$ dimer (open circles), Cpl-$1^{C45S,D324}$ dimer (open squares). All enzymes were tested at a concentration of 0.5 mg/ml. Each dot represents the mean value of 3 experiments.

Thirteen (13) Cpl-1C45S mutants were each engineered to have an additional cysteine at 13 different positions within the protein sequence. Among those, 6/13 mutants showed the same anti-microbial activity as native Cpl-1 when tested in their monomeric state in presence of 1 mM of DTT in the in vitro killing assay on S. pneumoniae DCC1490 (TABLE 1). As for all Cpl-1 mutants containing an exposed cysteine, spontaneous dimerization occurred after lactose induction of the corresponding 6 mutant lysins. We purified the corresponding dimers and tested their anti-microbial activities in our in vitro killing assay (FIG. 5). At 0.5 mg/ml, all dimers (except Cpl-1$^{C45S,D324C}$) showed ≥87.5% of reduction in their anti-microbial activities. Thus, dimerization at other positions than the very end of the C-terminal part dramatically impairs Cpl-1 enzymatic activity. These observations revealed the importance of good positioning of the new cysteine residue involved in the formation of the disulfide bridge between two monomers.

TABLE 1

Anti-Microbial Activities of Cpl-1 Mutants at 0.5 mg/ml

| Name of Mutant | % of Activity for Mutant Monomers | % of Activity for Purified Mutant Dimers |
| --- | --- | --- |
| Cpl-1$^{C45S;Q85C}$ | 100 | 0 |
| Cpl-1$^{C45S;D194C}$ | 100 | <1 |
| Cpl-1$^{C45S;S206C}$ | 25 | n.d |
| Cpl-1$^{C45S;N214C}$ | 100 | 5 |
| Cpl-1$^{C45S;G216C}$ | 100 | 3 |
| Cpl-1$^{C45S;F217C}$ | 25 | n.d |
| Cpl-1$^{C45S;E249C}$ | 75 | n.d |
| Cpl-1$^{C45S;D256C}$ | 100 | 12.5 |
| Cpl-1$^{C45S;S269C}$ | 100 | 3 |
| Cpl-1$^{C45S;M301C}$ | 18.75 | n.d |
| Cpl-1$^{C45S;G310C}$ | 75 | n.d |
| Cpl-1$^{C45S;N319C}$ | 50 | n.d |
| Cpl-1$^{C45S;D324C}$ | 100 | 100 | wt, wild-type,
n.d., not determined

Plasma Clearance of Cpl-1 and Cpl-1$^{C45S,D324C}$ Dimers in Mice

Figure 4:
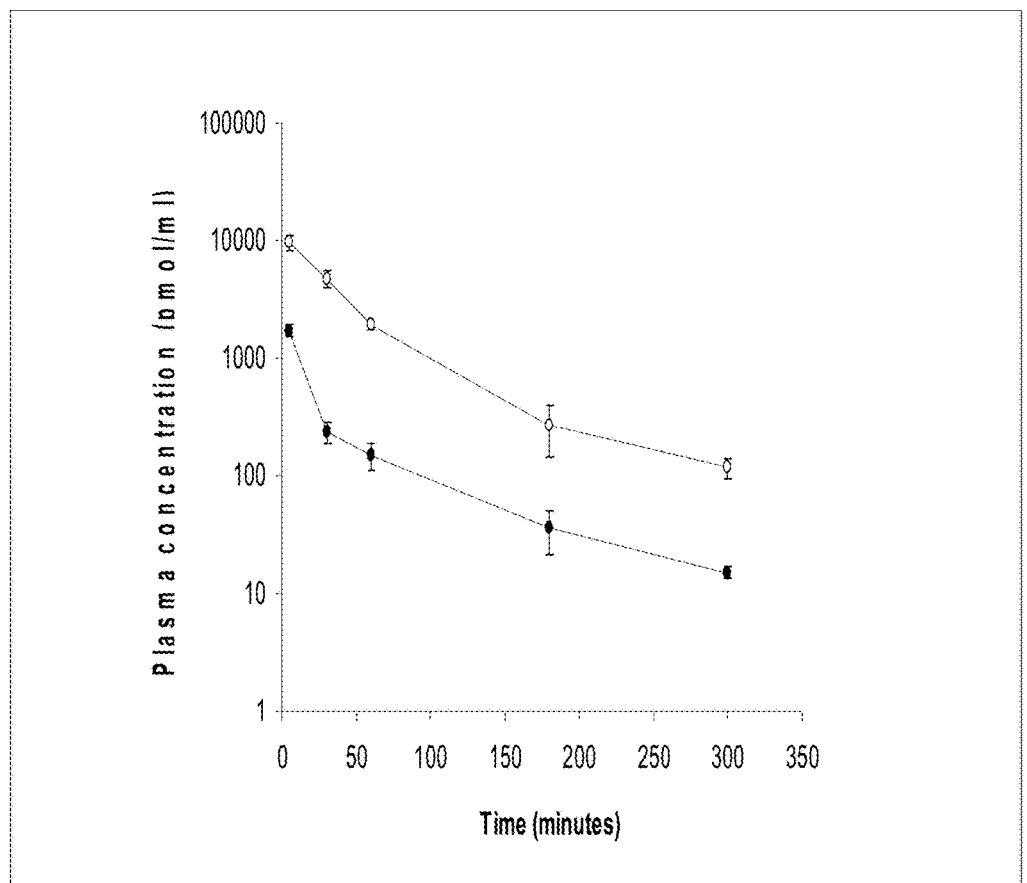
FIG. 4. Plasma clearance of enzybiotics in mice. Balb/c mice were injected with 12.16 nmoles in 100 µï PB 50 mM, pH 7.4 of either Cpl-1 (filled circles) or Cpl1$^{C45S,D324C}$ dimer (open circles), n=3 for each time point.

Balb/c mice were injected in the lateral tail vein with a bolus of 100 of either native Cpl-1 at 4.5 mg/ml (12.16 nmoles/100 µï) or Cpl-1$^{C45S,D324C}$ dimers at a concentration of 9 mg/ml (12.16 nmoles/100 µï). Blood samples were taken at 5, 30, 60, 180, and 300 minutes post-injection. Using a sandwich ELISA assay the concentration of the Cpl-1$^{C45S,D324C}$ dimers was found to be significantly higher than the control monomer at each time point (FIG. 4). For example, compared to the Cpl-1 monomer, 20.32 times more dimer molecules were detected in the plasma 30 minutes post-injection (4,764.32±788.55 versus 234.5±48.93 pmol/ml for Cpl-1$^{C45S,D324C}$ dimer and Cpl-1, respectively). After 5 hours the difference was 7.76 (116.8±22.85 versus 15.05±1.82 pmol/ml, for Cpl-1$^{C45S,D324C}$ dimer and Cpl-1, respectively). The calculated area under the curve (AUC) representing the residual lysin in plasma over the course of the experiment was 44.417 nmol/min$^-$ Vml$^{-1}$ for the monomer versus 435.026 nmol/min$^{-1}$/ml$^{-1}$ for the dimer. Thus, for the injected dose of 12.16 nmoles, clearance values of 0.274 ml/min$^{-1}$ were found for the Cpl-1 monomer compared to 0.028 ml/min$^{-1}$ for the Cpl-1$^{C45S,D324C}$ dimer, making the clearance of the stabilized dimers to be decreased by a factor of −9.8 over the monomer.

Doubling the size of the Cpl-1 by dimerization was found to have a significant effect on the clearance of the enzyme from the plasma of mice, suggesting that renal filtration could play a substantial role in its elimination. Our findings indicate that the Cpl-1$^{C45S,D324C}$ dimer is a far more potent intravenous molecule compared to the native Cpl-1 monomer previously tested in a mouse model of pneumococcal septicemia and shown to have a 20.5 minute half-life (12, 15). Moreover, a greater amount of dimer is available in the blood for systemic distribution and thus, the Cpl-1$^{C45S,D324C}$ dimer is expected to show improved therapeutic effects in other S. pneumoniae associated diseases. For example, in a recent publication, the monomeric form of Cpl-1 was used to cure mice of pneumonia by delivering the lysin intraperitoneally every 12 hours (31). The effectiveness of this treatment despite the short half-life of the lysin suggests that the dimeric form could prove to be significantly more effective in treating similar infections. Of course, bioavailability of the dimer at the infection site has to be evaluated in the in vivo setting.

In summary, we report herein the construction of a stabilized dimeric lysin that is twice more active in vitro than the original monomer (on a 1/1 molar ratio), and has a approximately 10-times greater bioavailability in the blood. We also present evidence that the choice of the position at which the neo-introduced cysteine involved in dimerization has to be introduced is critical. A long-lasting Cpl-1 lysin could represent anew alternative against both antibiotic-susceptible and -resistant pneumococci. Moreover, and because several other phage lysins have been shown or are suspected to dimerize (7, 24, 25), this strategy could represent a general way to increase the activity and/or pharmacokinetics of certain phage lysins.

REFERENCES

1. Borysowski, J., B. Weber-Dabrowska, and A. Gorski. 2006. Bacteriophage endolysins as a novel class of antibacterial agents. Exp Biol Med (Maywood) 231:366-77.
2. Biundage, J. F., and G. D. Shanks. 2008. Deaths from bacterial pneumonia during 1918-19 influenza pandemic. Emerg Infect Dis 14: 1193-9.
3. Biundage, J. F., and G. D. Shanks. 2007. What really happened during the 1918 influenza pandemic? The importance of bacterial secondary infections. J Infect Dis 196:1717-8; author reply 1718-9.
4. CDC. 2009. Pneumococcal diseases, p. 217-30. In W. Atkinson, S. Wolfe, J. Hamborsky, and L. McIntyre (ed.), Epidemiology and prevention of vaccine-preventable diseases (The Pink Book), 11th ed. Public Health Foundation, Washington DC.
5. English, M. 2000. Impact of bacterial pneumonias on world child health. Paediatr Respir Rev 1:21-5.
6. Entenza, J. M., J. M. Loeffler, D. Grandgirard, V. A. Fischetti, and P. Moreillon. 2005. Therapeutic effects of bacteriophage Cpl-1 lysin against Streptococcus pneumoniae endocarditis in rats. Antimicrob Agents Chemother 49:4789-92.
7. Fernandez-Tornero, C, E. Garcia, R. Lopez, G. Gimenez-Gallego, and A. Romero. 2002. Two new crystal forms of the choline-binding domain of the major pneumococcal autolysin: insights into the dynamics of the active homodimer. J Mol Biol 321:163-73.
8. File, T. M., Jr. 2004. Streptococcus pneumoniae and community-acquired pneumonia: a cause for concern. Am J Med 117 Suppl 3A:39S-50S.
9. Fischetti, V. A. 2008. Bacteriophage lysins as effective antibacterials. Curr Opin Microbiol 11:393-400.
10. Garcia, J. L., E. Garcia, A. Arraras, P. Garcia, C. Ronda, and R. Lopez. 1987. Cloning, purification, and biochemical characterization of the pneumococcal bacteriophage Cp-1 lysin. J Virol 61:2573-80.
11. Goossens, H. 2009. Antibiotic consumption and link to resistance. Clin Microbiol Infect 15 Suppl 3:12-5.
12. Grandgirard, D., J. M. Loeffler, V. A. Fischetti, and S. L. Leib. 2008. Phage lytic enzyme Cpl-1 for antibacterial therapy in experimental pneumococcal meningitis. J Infect Dis 197:1519-22.
13. Jacobs, M. R. 2004. Streptococcus pneumoniae: epidemiology and patterns of resistance. Am J Med 117 Suppl 3A:3S-155.
14. Jado, I., R. Lopez, E. Garcia, A. Fenoll, J. Casal, and P. Garcia. 2003. Phage lytic enzymes as therapy for antibiotic-resistant Streptococcus pneumoniae infection in a murine sepsis model. J Antimicrob Chemother 52:967-73.
15. Loeffler, J. M., S. Djurkovic, and V. A. Fischetti. 2003. Phage lytic enzyme Cpl-1 as a novel antimicrobial for pneumococcal bacteremia. Infect Immun 71:6199-204.

16. Loeffler, J. M., and V. A. Fischetti. 2003. Synergistic lethal effect of a combination of phage lytic enzymes with different activities on penicillin-sensitive and -resistant *Streptococcus pneumoniae* strains. Antimicrob Agents Chemother 47:375-7.
17. Loeffler, J. M., D. Nelson, and V. A. Fischetti. 2001. Rapid killing of *Streptococcus pneumoniae* with a bacteriophage cell wall hydrolase. Science 294:2170-2.
18. Maack, T., V. Johnson, S. T. Kau, J. Figueiredo, and D. Sigulem. 1979. Renal filtration, transport, and metabolism of low-molecular-weight proteins: a review. Kidney Int 16:251-70.
19. Mandell, L. A., L. R. Peterson, R. Wise, D. Hooper, D. E. Low, U. B. Schaad, K. P. Klugman, and P. Courvalin. 2002. The battle against emerging antibiotic resistance: should fluoroquinolones be used to treat children? Clin Infect Dis 35:721-7.
20. Morens, D. M., J. K. Taubenberger, and A. S. Fauci. 2009. The persistent legacy of the 1918 influenza virus. N Engl J Med 361:225-9.
21. Morens, D. M., J. K. Taubenberger, G. K. Folkers, and A. S. Fauci. 2009. An historical antecedent of modern guidelines for community pandemic influenza mitigation. Public Health Rep 124:22-5.
22. Perez-Dorado, I., N. E. Campillo, B. Monterroso, D. Hesek, M. Lee, J. A. Paez, P. Garcia, M. Martinez-Ripoll, J. L. Garcia, S. Mobashery, M. Menendez, and J. A. Hermoso. 2007. Elucidation of the molecular recognition of bacterial cell wall by modular pneumococcal phage endolysin CPL-1. J Biol Chem 282:24990-9.
23. Reinert, R. R. 2009. The public health ramifications of pneumococcal resistance. Clin Microbiol Infect 15 Suppl 3:1-3.
24. Romero, P., R. Lopez, and E. Garcia. 2004. Characterization of LytA-like N-acetylmuramoyl-L-alanine amidases from two new *Streptococcus mitis* bacteriophages provides insights into the properties of the major pneumococcal autolysin. J Bacteriol 186:8229-39.
25. Romero, P., R. Lopez, and E. Garcia. 2007. Key role of amino acid residues in the dimerization and catalytic activation of the autolysin LytA, an important virulence factor in *Streptococcus pneumoniae*. J Biol Chem 282: 17729-37.
26. Sanchez-Puelles, J. M., J. L. Garcia, R. Lopez, and E. Garcia. 1987. 3'-end modifications of the *Streptococcus pneumoniae* lytA gene: role of the carboxy terminus of the pneumococcal autolysin in the process of enzymatic activation (conversion). Gene 61:13-9.
27. Sulakvelidze, A., Z. Alavidze, and J. G. Morris, Jr. 2001. Bacteriophage therapy. Antimicrob Agents Chemother 45:649-59.
28. Sulakvelidze, A., and P. Barrow. 2005. Phage therapy in animals and agribusiness, p. 335-71. In E. Kutter and A. Sulakvelidze (ed.), Bacteriophages: Biology and Applications. CRC Press, USA.
29. Sulakvelidze, A., and E. Kutter. 2005. Bacteriophage therapy in humans, p. 381-426. In E. Kutter and A. Sulakvelidze (ed.), Bacteriophages: Biology and Applications. CRC Press, USA.
30. Varea, J., J. L. Saiz, C. Lopez-Zumel, B. Monterroso, F. J. Medrano, J. L. Arrondo, I. Iloro, J. Laynez, J. L. Garcia, and M. Menendez. 2000. Do sequence repeats play an equivalent role in the choline-binding module of pneumococcal LytA amidase? J Biol Chem 275:26842-55.
31. Witzenrath, M., B. Schmeck, J. M. Doehn, T. Tschernig, J. Zahlten, J. M. Loeffler, M. Zemlin, H. Muller, B. Gutbier, H. Schutte, S. Hippenstiel, V. A. Fischetti, N. Suttorp, and S. Rosseau. 2009. Systemic use of the endolysin Cpl-1 rescues mice with fatal pneumococcal pneumonia. Crit Care Med 37:642-9.

EXAMPLE 2

In Vivo Animal Studies

Intravenous killing efficacy. Four- to six-week-old female C3H/HeJ mice were infected through the tail vein with $3 \times 10^7$ CFU of log-phase *S. pneumoniae* serotype 14 (strain DCC1490, penicillin susceptible) and were treated with different concentrations (100-2000 ug) Cpl-1 in 100 ul or the same volume (100 ul) of buffer intravenously 10 h postinfection. Blood samples were obtained before and 15 and 120 min after treatment, and the bacterial titers were determined by serial dilution and plating on blood agar. The presence of *S. pneumoniae* in alpha-hemolytic colonies was confirmed by using optochin disks.

EXAMPLE 3

Dimerized Pal Enzyme

Pal is a Streptococcal lysin isolated from a pneumococcal bacteriophage that specifically digests pneumococcal cell wall within seconds (Loeffler, J M et al (2001) Science 294: 2170-2172; U.S. Pat. No. 7,569,223). Pal is a 296 amino acid lytic protein with a molecular mass of 34 kDa and is an amidase, cleaving the peptidoglycan between N-acetylmuramic acid and L-alanine. Cpl-1, described above, is a 339 amino acid protein and is a lysozyme, cleaving the glycosidic bond between N-acetylmuramic acid and N-acetylglucosamine (Garcia, P et al (1997) Microb Drug Resist 3:165-176). While both enzymes have very different N-terminal catalytic sites, they share a similar C-terminal cell wall attachment site, which binds to choline. The enhanced killing efficacy of a combination of Pal and Cpl-1 on *S. pneumoniae*, including penicillin resistant strains, has been described (Loeffler, J M and Fischetti, V A (2003) Antimicrob Agents and Chemoth 47(1):375-377; Published PCT WO2004/058182).

Like Cpl-1, the Pal enzyme C-terminal region includes choline binding repeats and C-terminal amino acids with correspondence to LytA, in fact 11 of the C-terminal 14 amino acids of Pal are identical to LytA sequence. When comparing Pal to Cpl-1, 9 of the C-terminal 14 amino acids of Pal are identical to Cpl-1. Pal shows overall similarity with Cpl-1 and LytA in its C-terminal region, particularly from amino acids 155 to 296, where 60 of these 142 amino acids are identical among Pal, Cpl-1 and LytA. FIG. 7 depicts the amino acid sequences of Cpl-1, Pal and LytA and demonstrates the homologous C-terminal regions of these three enzymes.

Using a comparable approach as described above for Cpl-1, Pal dimer composed of two monomers covalently linked and stabilized by a disulfide bond is engineered and constructed. Formation of a disulfide bridge between two monomers of Pal enzyme is used, as with Cpl-1, to generate exemplary pre-dimerized Pal enzyme.

The wild-type Pal enzyme contains three cysteine residues at amino acid positions 34, 113, and 250. Using the Accpro server under the SCRATCH protein predicator website (scratch.proteomics.ics.uci.edu/index), none of the Pal cysteine residues was predicted to be accessible to the solvent. Thus, it was not deemed necessary to engineer a Pal mutant lacking any of the native enzyme cysteines before proceeding to pre-dimerize Pal. To construct the pre-dimerized form of Pal, C terminal region amino acids are mutated to Cys. The new cysteine residue is specifically introduced prior to the final 14 amino-acid stretch in the C-terminal tail of Pal to prevent disturbance of any critical structure in this homologous region. Mutation is confirmed by DNA sequencing and wild type and mutant Pal overexpressed in *E. coli* DH5α cells and purified to homogeneity on a DEAE-Sepharose column. Pre-dimerized mutant Pal is confirmed by a second band appearing at about 70 kDa on Coomassie stained non-reducing SDS-PAGE gel. Reduction with 10 mM dithiothreitol (DTT), leading to the disappearance of the higher kDa band, confirms that the disulfide bond-related dimeric form of Pal is reducible. Pal$^{D280C}$ having amino acid 280 mutated to cysteine is constructed, confirmed and tested to establish production of pre-dimerized Pal enzyme. The Pal$^{D280C}$ mutant is analogous to Cpl-1$^{C45S,D324C}$ in being pre-dimerized at a comparable location adjacent to the LytA analogous C-terminal 14 amino acids of Pal. In vitro and in vivo testing of killing activity and efficacy of mutant dimerized Pal is conducted as above described for Cpl-1 to demonstrate anti-pneumococcal activity of mutant dimerized Pal.

While the invention has been described and illustrated herein by reference to various specific materials, procedures, and examples, it is understood that the invention is not restricted to the particular materials, combinations of materials, and procedures selected for that purpose. Numerous variations of such details can be implied and will be appreciated by those skilled in the art.

What is claimed is:

1. An isolated dimeric phage lysin comprising two phage lysin monomers specific for bacteria and capable of killing at least one or more *Streptococcus* bacteria covalently linked to each other, wherein said dimer has killing activity against one or more *Streptococcus* bacteria that is greater than the killing activity of any one of the phage lysin monomers, and wherein the lysin monomers are covalently associated or cross-linked via reactive groups or via amino acids in each monomer sequence at the C-terminus.

2. The lysin of claim 1, wherein said lysin monomers are Cpl-1 monomers having at least 90% amino acid sequence identity to unmutated Cpl-1 SEQ ID NO: 1, or are Pal monomers having at least 90% amino acid sequence identity to unmutated Pal SEQ ID NO: 5.

3. The lysin of claim 1, wherein said lysin monomers are chemically cross-linked to each other.

4. The lysin of claim 1, wherein said lysin monomers are covalently linked to each other by a disulfide bond.

5. The lysin of claim 4, wherein each monomer has a Cys residue that is between 14 and 20 amino acids from the C-terminus.

6. The lysin of claim 5, wherein said lysin monomers do not have a Cys residue in the first 45 residues.

7. The lysin of claim 1, wherein at least one of said lysin monomers comprise a catalytic domain of a first phage lysin specific for bacteria and capable of killing at least one or more *Streptococcus* bacteria and a binding domain of a second phage lysin specific for bacteria and capable of killing at least one or more *Streptococcus* bacteria.

8. The lysin of claim 7, wherein the catalytic domain of a first phage lysin is the catalytic domain of Cpl-1 lysin amino acids 1-190 of SEQ ID NO: 1.

9. The lysin of claim 7, wherein the binding domain of a second phage lysin is the binding domain of Cpl-1 lysin amino acids 191-326 of SEQ ID NO: 1, or the binding domain of Pal lysin amino acids 155-296 of SEQ ID NO: 5.

10. The lysin of claim 1 having killing activity against *Streptococcus pneumoniae*.

11. A method of treating a mammal suffering from a disease or condition caused by a streptococcal infection by administering a composition comprising a therapeutically effective amount of a lysin of claim 1.

12. The method of claim 11, wherein said infection is caused by *Streptococcus pneumoniae*.

13. The method of claim 11, wherein said disease or condition is one or more diseases or conditions selected from the group of bacteremia, meningitis, pneumonia, otitis media, and sinusitis.

14. A method for decolonizing streptococcus in a mammal suffering from or at risk of a disease or condition caused by a streptococcal infection by administering a composition comprising a therapeutically effective amount of a lysin of claim 1.

15. The method of claim 14, wherein said infection is caused by *Streptococcus pneumoniae*.

16. A pharmaceutical composition comprising a therapeutically effective amount of a dimeric lysin of claim 1, and a pharmaceutically acceptable carrier.

17. An anti-microbial composition for sanitizing or decontaminating porous or non-porous surfaces comprising a lysin of claim 1.

18. A method for decontaminating inanimate surfaces suspected of containing infectious bacteria comprising treatment of said surfaces with a bacteriocidally or bacteriostatically effective amount of the composition of claim 16.

19. The lysin of claim 1, wherein said dimer has a longer half-life or reduced plasma clearance than any one of the phage lysin monomers.

20. The lysin of claim 1, wherein said lysin monomers are cross-linked via a linker peptide or a heterologous peptide fused to their C-terminal ends or regions.

* * * * *

SEQUENCE LISTING

```
<160> NUMBER OF SEQ ID NOS: 6

<210> SEQ ID NO 1
<211> LENGTH: 339
<212> TYPE: PRT
<213> ORGANISM: Streptococcus pneumoniae

<400> SEQUENCE: 1

Met Val Lys Lys Asn Asp Leu Phe Val Asp Val Ser Ser His Asn Gly
1               5                   10                  15

Tyr Asp Ile Thr Gly Ile Leu Glu Gln Met Gly Thr Thr Asn Thr Ile
            20                  25                  30

Ile Lys Ile Ser Glu Ser Thr Thr Tyr Leu Asn Pro Cys Leu Ser Ala
        35                  40                  45

Gln Val Glu Gln Ser Asn Pro Ile Gly Phe Tyr His Phe Ala Arg Phe
    50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110

Gln Met Ile Ala Asp Ala Gly Tyr Lys Pro Ile Tyr Tyr Ser Tyr Lys
        115                 120                 125

Pro Phe Thr His Asp Asn Val Asp Tyr Gln Gln Ile Leu Ala Gln Phe
    130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
        195                 200                 205

Trp Trp Phe Arg Arg Asn Asn Gly Ser Phe Pro Tyr Asn Lys Trp Glu
    210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Asp Lys Trp Tyr Tyr Leu Lys Asp
                245                 250                 255

Asn Gly Ala Met Ala Thr Gly Trp Val Leu Val Gly Ser Glu Trp Tyr
```

-continued

```
                260                 265                 270
Tyr Met Asp Asp Ser Gly Ala Met Val Thr Gly Trp Val Lys Tyr Lys
            275                 280                 285

Asn Asn Trp Tyr Tyr Met Thr Asn Glu Arg Gly Asn Met Val Ser Asn
        290                 295                 300

Glu Phe Ile Lys Ser Gly Lys Gly Trp Tyr Phe Met Asn Thr Asn Gly
305                 310                 315                 320

Glu Leu Ala Asp Asn Pro Ser Phe Thr Lys Glu Pro Asp Gly Leu Ile
                325                 330                 335

Thr Val Ala

<210> SEQ ID NO 2
<211> LENGTH: 318
<212> TYPE: PRT
<213> ORGANISM: Streptococcus pneumoniae

<400> SEQUENCE: 2

Met Glu Ile Asn Val Ser Lys Leu Arg Thr Asp Leu Pro Gln Val Gly
1               5                   10                  15

Val Gln Pro Tyr Arg Gln Val His Ala His Ser Thr Gly Asn Pro His
            20                  25                  30

Ser Thr Val Gln Asn Glu Ala Asp Tyr His Trp Arg Lys Asp Pro Glu
        35                  40                  45

Leu Gly Phe Phe Ser His Ile Val Gly Asn Gly Cys Ile Met Gln Val
    50                  55                  60

Gly Pro Val Asp Asn Gly Ala Trp Asp Val Gly Gly Trp Asn Ala
65                  70                  75              80

Glu Thr Tyr Ala Ala Val Glu Leu Ile Glu Ser His Ser Thr Lys Glu
                85                  90                  95

Glu Phe Met Thr Asp Tyr Arg Leu Tyr Ile Glu Leu Leu Arg Asn Leu
            100                 105                 110

Ala Asp Glu Ala Gly Leu Pro Lys Thr Leu Asp Thr Gly Ser Leu Ala
        115                 120                 125

Gly Ile Lys Thr His Glu Tyr Cys Thr Asn Asn Gln Pro Asn Asn His
    130                 135                 140

Ser Asp His Val Asp Pro Tyr Pro Tyr Leu Ala Lys Trp Gly Ile Ser
145                 150                 155                 160

Arg Glu Gln Phe Lys His Asp Ile Glu Asn Gly Leu Thr Ile Glu Thr
                165                 170                 175

Gly Trp Gln Lys Asn Asp Thr Gly Tyr Trp Tyr Val His Ser Asp Gly
            180                 185                 190

Ser Tyr Pro Lys Asp Lys Phe Glu Lys Ile Asn Gly Thr Trp Tyr Tyr
        195                 200                 205

Phe Asp Ser Ser Gly Tyr Met Leu Ala Asp Arg Trp Arg Lys His Thr
    210                 215                 220

Asp Gly Asn Trp Tyr Trp Phe Asp Asn Ser Gly Glu Met Ala Thr Gly
225                 230                 235                 240

Trp Lys Lys Ile Ala Asp Lys Trp Tyr Tyr Phe Asn Glu Glu Gly Ala
                245                 250                 255

Met Lys Thr Gly Trp Val Lys Tyr Lys Asp Thr Trp Tyr Tyr Leu Asp
            260                 265                 270

Ala Lys Glu Gly Ala Met Val Ser Asn Ala Phe Ile Gln Ser Ala Asp
        275                 280                 285

Gly Thr Gly Trp Tyr Tyr Leu Lys Pro Asp Gly Thr Leu Ala Asp Lys
```

```
                290                 295                 300
Pro Glu Phe Thr Val Glu Pro Asp Gly Leu Ile Thr Val Lys
305                 310                 315

<210> SEQ ID NO 3
<211> LENGTH: 339
<212> TYPE: PRT
<213> ORGANISM: Streptococcus pneumoniae
<220> FEATURE:
<221> NAME/KEY: VARIANT
<222> LOCATION: (45)..(45)
<223> OTHER INFORMATION: serine for cysteine
<220> FEATURE:
<221> NAME/KEY: VARIANT
<222> LOCATION: (324)..(324)
<223> OTHER INFORMATION: cysteine for aspartic acid

<400> SEQUENCE: 3

Met Val Lys Lys Asn Asp Leu Phe Val Asp Val Ser His Asn Gly
1                5                  10                 15

Tyr Asp Ile Thr Gly Ile Leu Glu Gln Met Gly Thr Thr Asn Thr Ile
                20                  25                  30

Ile Lys Ile Ser Glu Ser Thr Thr Tyr Leu Asn Pro Ser Leu Ser Ala
            35                  40                  45

Gln Val Glu Gln Ser Asn Pro Ile Gly Phe Tyr His Phe Ala Arg Phe
        50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110

Gln Met Ile Ala Asp Ala Gly Tyr Lys Pro Ile Tyr Tyr Ser Tyr Lys
        115                 120                 125

Pro Phe Thr His Asp Asn Val Asp Tyr Gln Gln Ile Leu Ala Gln Phe
    130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
        195                 200                 205

Trp Trp Phe Arg Arg Asn Asn Gly Ser Phe Pro Tyr Asn Lys Trp Glu
    210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Asp Lys Trp Tyr Tyr Leu Lys Asp
                245                 250                 255

Asn Gly Ala Met Ala Thr Gly Trp Val Leu Val Gly Ser Glu Trp Tyr
            260                 265                 270

Tyr Met Asp Asp Ser Gly Ala Met Val Thr Gly Trp Val Lys Tyr Lys
        275                 280                 285

Asn Asn Trp Tyr Tyr Met Thr Asn Glu Arg Gly Asn Met Val Ser Asn
    290                 295                 300

Glu Phe Ile Lys Ser Gly Lys Gly Trp Tyr Phe Met Asn Thr Asn Gly
```

```
305                 310                 315                 320

Glu Leu Ala Cys Asn Pro Ser Phe Thr Lys Glu Pro Asp Gly Leu Ile
                325                 330                 335

Thr Val Ala

<210> SEQ ID NO 4
<211> LENGTH: 339
<212> TYPE: PRT
<213> ORGANISM: Streptococcus pneumoniae
<220> FEATURE:
<221> NAME/KEY: VARIANT
<222> LOCATION: (45)..(45)
<223> OTHER INFORMATION: serine for cysteine

<400> SEQUENCE: 4

Met Val Lys Lys Asn Asp Leu Phe Val Asp Val Ser His Asn Gly
 1               5                  10                  15

Tyr Asp Ile Thr Gly Ile Leu Glu Gln Met Gly Thr Thr Asn Thr Ile
                20                  25                  30

Ile Lys Ile Ser Glu Ser Thr Thr Tyr Leu Asn Pro Ser Leu Ser Ala
                35                  40                  45

Gln Val Glu Gln Ser Asn Pro Ile Gly Phe Tyr His Phe Ala Arg Phe
 50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
                100                 105                 110

Gln Met Ile Ala Asp Ala Gly Tyr Lys Pro Ile Tyr Tyr Ser Tyr Lys
                115                 120                 125

Pro Phe Thr His Asp Asn Val Asp Tyr Gln Gln Ile Leu Ala Gln Phe
                130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
                180                 185                 190

Asp Asp Lys Pro Lys Thr Ala Gly Thr Trp Lys Gln Asp Ser Lys Gly
                195                 200                 205

Trp Trp Phe Arg Arg Asn Asn Gly Ser Phe Pro Tyr Asn Lys Trp Glu
                210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Asp Lys Trp Tyr Tyr Leu Lys Asp
                245                 250                 255

Asn Gly Ala Met Ala Thr Gly Trp Val Leu Val Gly Ser Glu Trp Tyr
                260                 265                 270

Tyr Met Asp Asp Ser Gly Ala Met Val Thr Gly Trp Val Lys Tyr Lys
                275                 280                 285

Asn Asn Trp Tyr Tyr Met Thr Asn Glu Arg Gly Asn Met Val Ser Asn
                290                 295                 300

Glu Phe Ile Lys Ser Gly Lys Gly Trp Tyr Phe Met Asn Thr Asn Gly
305                 310                 315                 320
```

```
Glu Leu Ala Asp Asn Pro Ser Phe Thr Lys Glu Pro Asp Gly Leu Ile
                325                 330                 335

Thr Val Ala

<210> SEQ ID NO 5
<211> LENGTH: 296
<212> TYPE: PRT
<213> ORGANISM: Streptococcus pneumoniae

<400> SEQUENCE: 5

Met Gly Val Asp Ile Glu Lys Gly Val Ala Trp Met Gln Ala Arg Lys
1               5                   10                  15

Gly Arg Val Ser Tyr Ser Met Asp Phe Arg Asp Gly Pro Asp Ser Tyr
                20                  25                  30

Asp Cys Ser Ser Ser Met Tyr Tyr Ala Leu Arg Ser Ala Gly Ala Ser
            35                  40                  45

Ser Ala Gly Trp Ala Val Asn Thr Glu Tyr Met His Ala Trp Leu Ile
        50                  55                  60

Glu Asn Gly Tyr Glu Leu Ile Ser Glu Asn Ala Pro Trp Asp Ala Lys
65                  70                  75                  80

Arg Gly Asp Ile Phe Ile Trp Gly Arg Lys Gly Ala Ser Ala Gly Ala
                85                  90                  95

Gly Gly His Thr Gly Met Phe Ile Asp Ser Asp Asn Ile Ile His Cys
            100                 105                 110

Asn Tyr Ala Tyr Asp Gly Ile Ser Val Asn Asp His Asp Glu Arg Trp
        115                 120                 125

Tyr Tyr Ala Gly Gln Pro Tyr Tyr Val Tyr Arg Leu Thr Asn Ala
    130                 135                 140

Asn Ala Gln Pro Ala Glu Lys Lys Leu Gly Trp Gln Lys Asp Ala Thr
145                 150                 155                 160

Gly Phe Trp Tyr Ala Arg Ala Asn Gly Thr Tyr Pro Lys Asp Glu Phe
                165                 170                 175

Glu Tyr Ile Glu Glu Asn Lys Ser Trp Phe Tyr Phe Asp Asp Gln Gly
            180                 185                 190

Tyr Met Leu Ala Glu Lys Trp Leu Lys His Thr Asp Gly Asn Trp Tyr
        195                 200                 205

Trp Phe Asp Arg Asp Gly Tyr Met Ala Thr Ser Trp Lys Arg Ile Gly
    210                 215                 220

Glu Ser Trp Tyr Tyr Phe Asn Arg Asp Gly Ser Met Val Thr Gly Trp
225                 230                 235                 240

Ile Lys Tyr Tyr Asp Asn Trp Tyr Tyr Cys Asp Ala Thr Asn Gly Asp
                245                 250                 255

Met Lys Ser Asn Ala Phe Ile Arg Tyr Asn Asp Gly Tyr Leu Leu
            260                 265                 270

Leu Pro Asp Gly Arg Leu Ala Asp Lys Pro Gln Phe Thr Val Glu Pro
        275                 280                 285

Asp Gly Leu Ile Thr Ala Lys Val
    290                 295

<210> SEQ ID NO 6
<211> LENGTH: 296
<212> TYPE: PRT
<213> ORGANISM: Streptococcus pneumoniae
<220> FEATURE:
<221> NAME/KEY: VARIANT
<222> LOCATION: (280)..(280)
<223> OTHER INFORMATION: cysteine for aspartic acid
```

<400> SEQUENCE: 6

```
Met Gly Val Asp Ile Glu Lys Gly Val Ala Trp Met Gln Ala Arg Lys
1               5                   10                  15

Gly Arg Val Ser Tyr Ser Met Asp Phe Arg Asp Gly Pro Asp Ser Tyr
            20                  25                  30

Asp Cys Ser Ser Ser Met Tyr Tyr Ala Leu Arg Ser Ala Gly Ala Ser
                35                  40                  45

Ser Ala Gly Trp Ala Val Asn Thr Glu Tyr Met His Ala Trp Leu Ile
    50                  55                  60

Glu Asn Gly Tyr Glu Leu Ile Ser Glu Asn Ala Pro Trp Asp Ala Lys
65                      70                  75                  80

Arg Gly Asp Ile Phe Ile Trp Gly Arg Lys Gly Ala Ser Ala Gly Ala
                85                  90                  95

Gly Gly His Thr Gly Met Phe Ile Asp Ser Asp Asn Ile Ile His Cys
                100                 105                 110

Asn Tyr Ala Tyr Asp Gly Ile Ser Val Asn Asp His Asp Glu Arg Trp
            115                 120                 125

Tyr Tyr Ala Gly Gln Pro Tyr Tyr Tyr Val Tyr Arg Leu Thr Asn Ala
    130                 135                 140

Asn Ala Gln Pro Ala Glu Lys Lys Leu Gly Trp Gln Lys Asp Ala Thr
145                 150                 155                 160

Gly Phe Trp Tyr Ala Arg Ala Asn Gly Thr Tyr Pro Lys Asp Glu Phe
                165                 170                 175

Glu Tyr Ile Glu Glu Asn Lys Ser Trp Phe Tyr Phe Asp Asp Gln Gly
                180                 185                 190

Tyr Met Leu Ala Glu Lys Trp Leu Lys His Thr Asp Gly Asn Trp Tyr
    195                 200                 205

Trp Phe Asp Arg Asp Gly Tyr Met Ala Thr Ser Trp Lys Arg Ile Gly
    210                 215                 220

Glu Ser Trp Tyr Tyr Phe Asn Arg Asp Gly Ser Met Val Thr Gly Trp
225                 230                 235                 240

Ile Lys Tyr Tyr Asp Asn Trp Tyr Tyr Cys Asp Ala Thr Asn Gly Asp
                245                 250                 255

Met Lys Ser Asn Ala Phe Ile Arg Tyr Asn Asp Gly Trp Tyr Leu Leu
                260                 265                 270

Leu Pro Asp Gly Arg Leu Ala Cys Lys Pro Gln Phe Thr Val Glu Pro
            275                 280                 285

Asp Gly Leu Ile Thr Ala Lys Val
            290                 295
```